(12) United States Patent
Ghani et al.

(10) Patent No.: US 12,329,577 B2
(45) Date of Patent: Jun. 17, 2025

(54) ULTRASOUND IMAGING

(71) Applicant: KONINKLIJKE PHILIPS N.V., Eindhoven (NL)

(72) Inventors: Muhammad Usman Ghani, Boston, MA (US); Hyeonwoo Lee, Cambridge, MA (US); Jonathan Fincke, Belmont, MA (US); Balasundar Iyyavu Raju, North Andover, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 94 days.

(21) Appl. No.: 18/131,396

(22) Filed: Apr. 6, 2023

(65) Prior Publication Data
US 2023/0329674 A1    Oct. 19, 2023

Related U.S. Application Data

(60) Provisional application No. 63/332,366, filed on Apr. 19, 2022.

(30) Foreign Application Priority Data

May 17, 2022   (EP) .................................... 22173748

(51) Int. Cl.
*A61B 8/00* (2006.01)
*G06T 7/00* (2017.01)

(52) U.S. Cl.
CPC ............ *A61B 8/4488* (2013.01); *A61B 8/461* (2013.01); *G06T 7/0012* (2013.01)

(58) Field of Classification Search
CPC ...... A61B 8/4488; A61B 8/461; G06T 7/0012
See application file for complete search history.

(56) References Cited

U.S. PATENT DOCUMENTS

| 7,672,491 B2 | 3/2010 | Krishnan et al. |
|---|---|---|
| 10,217,213 B2 | 2/2019 | Blackbourne et al. |
| (Continued) | | |

FOREIGN PATENT DOCUMENTS

| CN | 112990359 A | 6/2021 |
|---|---|---|
| EP | 3711673 A1 | 9/2020 |
| (Continued) | | |

OTHER PUBLICATIONS

International Search Report and Written Opinion for PCT/EP2023/059075; Mailing date: Jul. 7, 2023, 18 pages.

*Primary Examiner* — Dixomara Vargas

(57) ABSTRACT

An ultrasound system includes a processor and an ultrasound transducer array. The processor receives a first ultrasound image and a second ultrasound (1320) image from the transducer array. The first and second ultrasound images may be perpendicular to one another. The processor generates a score associated with the first ultrasound image and compares the score to a threshold score. Based on the score not satisfying the threshold score, the processor then determines a new imaging plane and directs the transducer array to obtain a third ultrasound image (1410) according to the new imaging plane. The third ultrasound image may also be perpendicular to the second ultrasound image. The processor circuit then displays the third ultrasound image and the second ultrasound image. The processor circuit also identifies an angle corresponding to the new imaging plane and displays an indicator (1342) overlaid over the second ultrasound image identifying the new imaging plane of the third ultrasound image.

14 Claims, 17 Drawing Sheets

(56) References Cited

U.S. PATENT DOCUMENTS

| | | | |
|---|---|---|---|
| 2019/0130554 A1* | 5/2019 | Rothberg | G06T 7/0002 |
| 2020/0121294 A1* | 4/2020 | Tsymbalenko | A61B 8/5246 |
| 2020/0315587 A1 | 10/2020 | Toporek et al. | |
| 2021/0042878 A1* | 2/2021 | Ghose | G06T 7/33 |
| 2021/0077060 A1* | 3/2021 | Kim | A61B 8/5269 |
| 2021/0128114 A1 | 5/2021 | Patil et al. | |
| 2021/0145411 A1* | 5/2021 | Aladahalli | A61B 8/54 |
| 2022/0087644 A1* | 3/2022 | Patil | A61B 8/463 |
| 2022/0196771 A1* | 6/2022 | Zur | G06N 3/08 |
| 2022/0222825 A1* | 7/2022 | Yaacobi | G06T 7/11 |

FOREIGN PATENT DOCUMENTS

| | | |
|---|---|---|
| WO | 2020225240 A1 | 11/2020 |
| WO | 2021099278 A1 | 5/2021 |

\* cited by examiner

ULTRASOUND IMAGING

CROSS-REFERENCE TO RELATED APPLICATIONS

This application claims the benefit and priority of Application No. 63/332,366 filed on Apr. 19, 2022, and European Application No. 22173748.9, filed May 17, 2022, all of which are hereby incorporated herein by reference herein.

FIELD OF THE INVENTION

The present disclosure relates generally to ultrasound imaging. In particular, an ultrasound system controls an ultrasound transducer array to obtain an image according to a set of imaging parameters, identifies anatomical feature(s) in the obtained ultrasound image, determines a set of adjusted parameters based on the identified anatomical feature(s), and controls the transducer array to obtain an additional image with the set of adjusted parameters.

BACKGROUND OF THE INVENTION

Physicians use many different medical diagnostic systems and tools to monitor a subject's health and diagnose and treat medical conditions. Ultrasound imaging systems are widely used for medical imaging and measurement. The ultrasound transducer probe may include an array of ultrasound transducer elements that transmit acoustic waves into a subject's body and record acoustic waves reflected from the internal anatomical structures within the subject's body, which may include tissues, blood vessels, and internal organs. The transmission and reception of acoustic waves, along with various beamforming and processing techniques, create an image of the subject's internal anatomical structures.

Ultrasound imaging is a safe, useful, and in some applications, non-invasive tool for diagnostic examination, interventions and/or treatment. Ultrasound imaging can provide insights into an anatomy before a surgery or other major procedure is performed as well as monitor and/or track changes to a particular anatomical feature over time. Many ultrasound imaging systems capture and/or calculate dimensions of anatomical structures during an ultrasound examination.

To make accurate measurements of a subject's anatomy or to properly diagnose various conditions based on ultrasound images, ultrasound images must be obtained with sufficient quality. The images obtained must be obtained so as to fully and clearly display any necessary structures for medical diagnosis, such as organs. To fully and clearly display the needed regions of the patient anatomy, a correct imaging orientation and plane must be used, a proper depth setting must be selected and a proper gain setting must be selected. Obtaining ultrasound images according with these proper settings often requires a high level of expertise by the user as well as optimal conditions for the procedure, including sufficient time and resources. A lack of expertise, time or resources can easily lead to poor quality ultrasound images and inaccurate measurements and diagnoses as a result.

SUMMARY OF THE INVENTION

The invention is defined by the independent claims. The dependent claims define advantageous embodiments.

Aspects of the present disclosure are systems, devices, and methods for automatically analyzing the image quality of ultrasound images and automatically adjusting ultrasound imaging parameters to improve image quality. Imaging parameters can also be referred to as imaging settings. Aspects of the present disclosure advantageously increase ultrasound image quality and subsequent accuracy of measurements and diagnoses when conditions of the imaging procedure are not ideal. For example, some ultrasound imaging procedures occur in an emergency or trauma scenario to assess internal bleeding of a subject, such as medical patient. In such cases, time is limited, and efficiency and accuracy are critical. In addition, the surrounding environment of the imaging procedure may be one in which cleanliness of the workspace is impeded by large amounts of blood or other unsanitary substances preventing a sonographer from quickly adjusting settings of the ultrasound system. By automatically adjusting settings to optimize image quality, the sonographer may be able to operate the ultrasound system with one hand as well as quickly and efficiently acquire the data to make an accurate diagnosis. Additional advantages of the present disclosure include assisting untrained users to obtain accurate images. In addition, people benefit from faster and more accurate imaging examinations and reduced number of re-scans required to get accurate data on a first attempt.

In some aspects, the ultrasound imaging system receives an ultrasound image from a probe. The system then analyses the image and assigns one or more classifications or scores to the image. These classifications or scores may correspond to the extent to which anatomical features are present within the image (e.g., a percentage of the feature displayed within the image) as well as other aspects of image quality such as a level of saturation affected by a gain setting. The system determines whether the image is of sufficient quality. If the image is of sufficient image quality, additional images may be received and analyzed in like manner. However, if the image quality is not sufficient, the system may identify which settings need to be adjusted based on the one or more classifications or scores. The system may then automatically adjust a depth setting, a lateral angle setting, a 3D elevational plane setting, or a gain setting and acquire an additional ultrasound image with the new settings. The system may then analyze and classify or score the new image to again determine whether it is of sufficient image quality and then again readjust settings if necessary or receive additional ultrasound images. In this way, ultrasound images acquired during an ultrasound imaging procedure are optimized automatically by the ultrasound imaging system to ensure that proper measurements and diagnoses can be made in a variety of user cases.

According to a first exemplary aspect, an ultrasound system is provided, which includes a processor configured for communication with a transducer array and a display, wherein the processor is configured to: control the transducer array to obtain a first ultrasound image with a first imaging plane; control the transducer array to obtain a second ultrasound image with a second imaging plane, wherein the second imaging plane and the first imaging plane are perpendicular; generate a score associated with the first ultrasound image; compare the score to a threshold score; automatically determine, based on the score not satisfying the threshold score, a third imaging plane for a third ultrasound image, wherein the second imaging plane and the third imaging plane are perpendicular; control the transducer array to obtain the third ultrasound image with the third imaging plane; and output, to the display, a screen display comprising: the second ultrasound image; the third ultrasound image; and an indicator overlaid on the second ultrasound image and configured to identify the third imaging plane.

In some aspects, a beam steering angle of the third imaging plane is different than the beam steering angle of the first ultrasound image. In some aspects, to control the transducer array to obtain the third ultrasound image, the processor is configured to output a signal to change the beam steering angle of the first ultrasound image to the beam steering angle of the third imaging plane. In some aspects, the second ultrasound image comprises an elevational view of the anatomical feature, and the third ultrasound image comprises a lateral view of the anatomical feature. In some aspects, the screen display further comprises an imaging plane graphic, wherein the imaging plane graphic is configured to identify the first imaging plane, the second imaging plane, and the third imaging plane. In some aspects, the imaging plane graphic comprises a first graphical representation of the first imaging plane, a second graphical representation of the second imaging plane, and a third graphical representation of the third imaging plane, the second graphical representation and the first graphical representation are perpendicular, and the second graphical representation and the third graphical representation are perpendicular. In some aspects, a position of the first graphical representation and a position of the third graphical representation are spaced along the second graphical representation such that the position of the first graphical representation and the position of the third graphical representation represent that the beam steering angle of the first imaging plane is different than the beam steering angle of the third ultrasound image.

According to a second exemplary aspect, an ultrasound system is provided, which includes a processor configured for communication with a transducer array of an ultrasound imaging probe and a display, wherein the processor is configured to: control the transducer array to obtain a first ultrasound image with a first set of one or more ultrasound parameters, wherein the first ultrasound image comprises a view of a subject anatomy; identify an anatomical feature of the subject anatomy within the first ultrasound image; generate, using a machine learning algorithm, a first score associated with the first ultrasound image, wherein the machine learning algorithm is trained using a reference ultrasound image; compare the first score to a threshold score; automatically determine, based on the first score not satisfying the threshold score, a second set of one or more ultrasound parameters; and control the transducer array to obtain a second ultrasound image with the second set of one or more ultrasound parameters.

In some aspects, the first score associated with the first ultrasound image is based on a measurement of the first ultrasound image. In some aspects, the measurement of the first ultrasound image comprises at least one of: a measurement of completeness of view of the anatomical feature; or a measurement of gain of the first ultrasound image. In some aspects, the one or more ultrasound parameters comprise at least one of: a depth parameter; a lateral view parameter; an angle of an elevational plane; or a gain parameter. In some aspects, the processor is configured to determine a second score associated with the second ultrasound image. In some aspects, based on the second score satisfying the threshold value, the processor is configured to store the second ultrasound image in a memory in communication with the processor. In some aspects, based on the second score not satisfying the threshold value, the processor is configured to: automatically determine a third set of one or more ultrasound parameters; and control ultrasound the transducer array to obtain a third ultrasound image. In some aspects, the first ultrasound image is one of a plurality of ultrasound images obtained during live imaging. In some aspects, the processor is further configured to determine a score corresponding to each of the plurality of ultrasound images. In some aspects, the processor is further configured to: automatically determine a second score associated with a second ultrasound image of the plurality of ultrasound images, wherein the first ultrasound image and the second ultrasound image are separated by a predetermined time period. In some aspects, the processor is further configured to output, to a display in communication with the processor, at least one of the first ultrasound image or the second ultrasound image.

In another exemplary aspect, a method is provided, which includes controlling a transducer array to obtain a first ultrasound image with a first set of one or more ultrasound parameters, wherein the first ultrasound image comprises a view of a subject anatomy; identifying an anatomical feature of the subject anatomy within the first ultrasound image; generating, using a machine learning algorithm, a score associated with the first ultrasound image, wherein the machine learning algorithm is trained using a reference ultrasound image; comparing the score to a threshold score; automatically determining, based on the score not satisfying the threshold score, a second set of one or more ultrasound parameters; and controlling the transducer array to obtain a second ultrasound image with the second set of one or more ultrasound parameters.

Additional aspects, features, and advantages of the present disclosure will become apparent from the following detailed description.

BRIEF DESCRIPTION OF THE DRAWINGS

Illustrative aspects of the present disclosure will be described with reference to the accompanying drawings, of which.

DETAILED DESCRIPTION OF EMBODIMENTS

Figure 1:
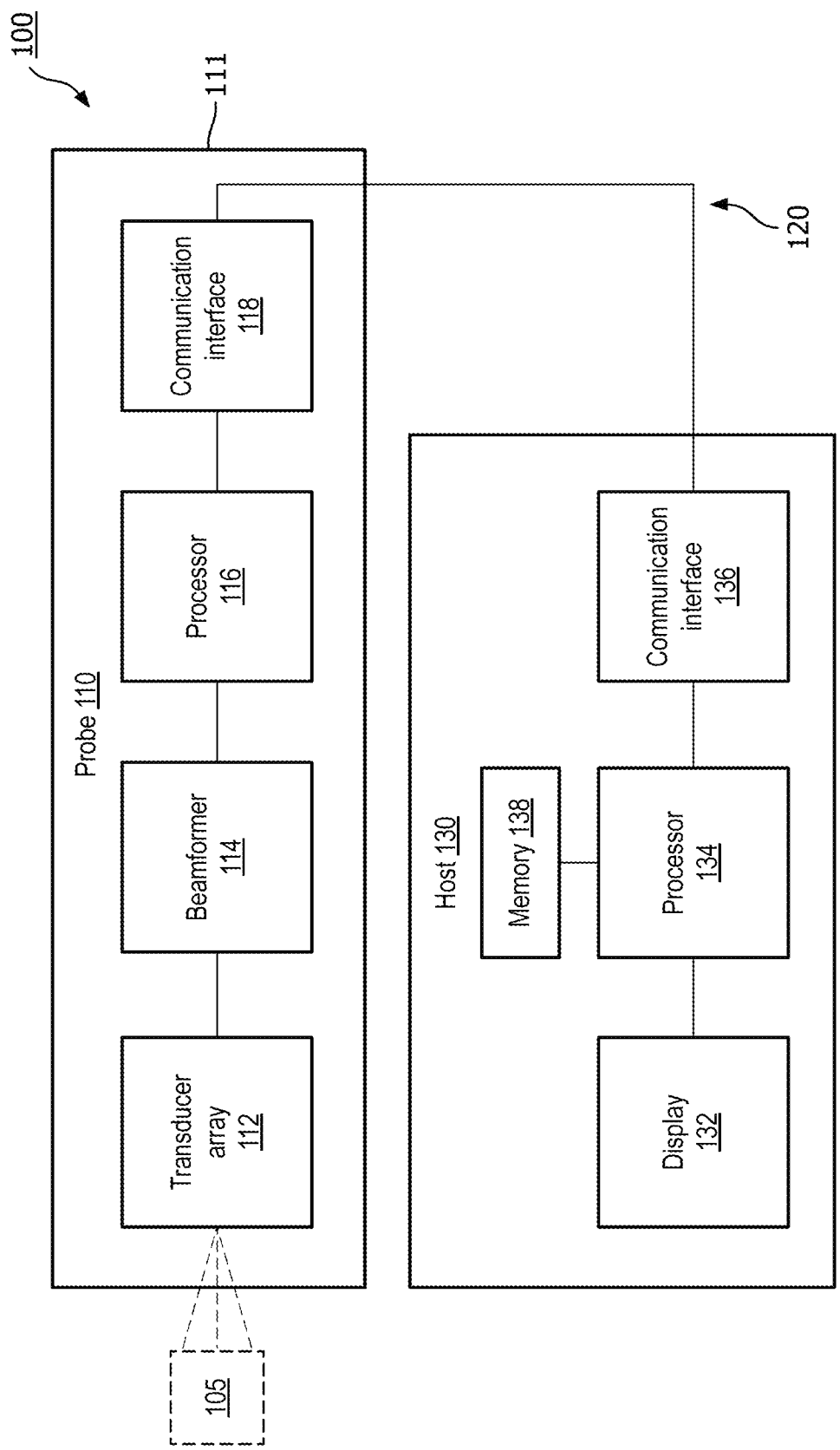
FIG. 1 is a schematic diagram of an ultrasound imaging system, according to aspects of the present disclosure.

For the purposes of promoting an understanding of the principles of the present disclosure, reference will now be made to the aspects illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one aspect may be combined with the features, components, and/or steps described with respect to other aspects of the present disclosure. For the sake of brevity, however, the numerous iterations of these combinations will not be described separately.

FIG. 1 is a schematic diagram of an ultrasound imaging system 100, according to aspects of the present disclosure. The system 100 is used for scanning an area or volume of a subject's body. A subject may include a patient of an ultrasound imaging procedure, or any other person, or any suitable living or non-living organism or structure. The system 100 includes an ultrasound imaging probe 110 in communication with a host 130 over a communication interface or link 120. The probe 110 may include a transducer array 112, a beamformer 114, a processor circuit 116, and a communication interface 118. The host 130 may include a display 132, a processor circuit 134, a communication interface 136, and a memory 138 storing subject information.

In some aspects, the probe 110 is an external ultrasound imaging device including a housing 111 configured for handheld operation by a user. The transducer array 112 can be configured to obtain ultrasound data while the user grasps the housing 111 of the probe 110 such that the transducer array 112 is positioned adjacent to or in contact with a subject's skin. The probe 110 is configured to obtain ultrasound data of anatomy within the subject's body while the probe 110 is positioned outside of the subject's body. The probe 110 can be an external ultrasound probe and/or a transthoracic echocardiography (TTE) probe.

The probe 110 can be an internal ultrasound imaging device and may comprise a housing 111 configured to be positioned within a lumen of a subject's body, including the subject's coronary vasculature, peripheral vasculature, esophagus, heart chamber, or other body lumen or body cavity. The probe 110 may be an intravascular ultrasound (IVUS) imaging catheter or an intracardiac echocardiography (ICE) catheter. In other aspects, probe 110 may be a transesophageal echocardiography (TEE) probe. Probe 110 may be of any suitable form for any suitable ultrasound imaging application including both external and internal ultrasound imaging.

Aspects of the present disclosure can be implemented with medical images of subjects obtained using any suitable medical imaging device and/or modality. Examples of medical images and medical imaging devices include x-ray images (angiographic images, fluoroscopic images, images with or without contrast) obtained by an x-ray imaging device, computed tomography (CT) images obtained by a CT imaging device, positron emission tomography-computed tomography (PET-CT) images obtained by a PET-CT imaging device, magnetic resonance images (MRI) obtained by an MRI device, single-photon emission computed tomography (SPECT) images obtained by a SPECT imaging device, optical coherence tomography (OCT) images obtained by an OCT imaging device, and intravascular photoacoustic (IVPA) images obtained by an IVPA imaging device. The medical imaging device can obtain the medical images while positioned outside the subject body, spaced from the subject body, adjacent to the subject body, in contact with the subject body, and/or inside the subject body.

For an ultrasound imaging device, the transducer array 112 emits ultrasound signals towards an anatomical object 105 of a subject and receives echo signals reflected from the object 105 back to the transducer array 112. The ultrasound transducer array 112 can include any suitable number of acoustic elements, including one or more acoustic elements and/or a plurality of acoustic elements. In some instances, the transducer array 112 includes a single acoustic element. The transducer array 112 may include an array of acoustic elements with any number of acoustic elements in any suitable configuration. For example, the transducer array 112 can include between 1 acoustic element and 10000 acoustic elements, including values such as 2 acoustic elements, 4 acoustic elements, 36 acoustic elements, 64 acoustic elements, 128 acoustic elements, 500 acoustic elements, 812 acoustic elements, 1000 acoustic elements, 3000 acoustic elements, 8000 acoustic elements, and/or other values both larger and smaller. The transducer array 112 may include an array of acoustic elements with any number of acoustic elements in any suitable configuration, such as a linear array, a planar array, a curved array, a curvilinear array, a circumferential array, an annular array, a phased array, a matrix array, a one-dimensional (1D) array, a 1.x-dimensional array (e.g., a 1.5D array), or a two-dimensional (2D) array. The array of acoustic elements (e.g., one or more rows, one or more columns, and/or one or more orientations) can be uniformly or independently controlled and activated. The transducer array 112 can be configured to obtain one-dimensional, two-dimensional, and/or three-dimensional images of a subject's anatomy. The transducer array 112 may include a piezoelectric micromachined ultrasound transducer (PMUT), capacitive micromachined ultrasonic transducer (CMUT), single crystal, lead zirconate titanate (PZT), PZT composite, other suitable transducer types, and/or combinations thereof.

The object 105 may include any anatomy or anatomical feature, such as blood vessels, nerve fibers, airways, mitral leaflets, cardiac structure, abdominal tissue structure, appendix, large intestine (or colon), small intestine, kidney, liver, and/or any other anatomy of a subject. For example, the object 105 can be a heart, including one or more chambers of the heart (e.g., left atrium, left ventricle, right atrium, right ventricle), heart muscle defining one or more of the chambers, valves (e.g., mitral valve, tricuspid valve, pulmonary valve, etc.), and other structure of the heart. The object 105 may include at least a portion of a subject's large intestine, small intestine, cecum pouch, appendix, terminal ileum, liver, epigastrium, and/or psoas muscle. The present disclosure can be implemented in the context of any number of anatomical locations and tissue types, including without limitation, organs including the liver, heart, kidneys, gall bladder, pancreas, lungs; ducts; intestines; nervous system structures including the brain, dural sac, spinal cord and peripheral nerves; the urinary tract; as well as valves within the blood vessels, blood, chambers or other parts of the heart, abdominal organs, and/or other systems of the body. The object 105 may include malignancies such as tumors, cysts, lesions, hemorrhages, or blood pools within any part of human anatomy. The anatomy may be a blood vessel, as an artery or a vein of a subject's vascular system, including cardiac vasculature, peripheral vasculature, neural vasculature, renal vasculature, and/or any other suitable lumen inside the body. In addition to natural structures, the present disclosure can be implemented in the context of man-made structures such as, but without limitation, heart valves, stents, shunts, filters, implants and other devices.

The beamformer 114 is coupled to the transducer array 112. The beamformer 114 controls the transducer array 112, for example, for transmission of the ultrasound signals and reception of the ultrasound echo signals. The beamformer 114 may apply a time-delay to signals sent to individual acoustic transducers within an array in the transducer 112 such that an acoustic signal is steered in any suitable direction propagating away from the probe 110. The beamformer 114 may further provide image signals to the processor circuit 116 based on the response of the received ultrasound echo signals. The beamformer 114 may include multiple stages of beamforming. The beamforming can reduce the number of signal lines for coupling to the processor circuit 116. The transducer array 112 in combination with the beamformer 114 may be referred to as an ultrasound imaging component.

The processor 116 is coupled to the beamformer 114. The processor 116 may also be described as a processor circuit, which can include other components in communication with the processor 116, such as a memory, beamformer 114, communication interface 118, and/or other suitable components. The processor 116 may include a central processing unit (CPU), a graphical processing unit (GPU), a digital signal processor (DSP), an application specific integrated circuit (ASIC), a controller, a field programmable gate array (FPGA) device, another hardware device, a firmware device, or any combination thereof configured to perform the operations described herein. The processor 116 may also be implemented as a combination of computing devices, e.g., a combination of a DSP and a microprocessor, a plurality of microprocessors, one or more microprocessors in conjunction with a DSP core, or any other such configuration. The processor 116 is configured to process the beamformed image signals. For example, the processor 116 may perform filtering and/or quadrature demodulation to condition the image signals. The processor 116 and/or 134 can be configured to control the array 112 to obtain ultrasound data associated with the object 105.

The communication interface 118 is coupled to the processor 116. The communication interface 118 may include one or more transmitters, one or more receivers, one or more transceivers, and/or circuitry for transmitting and/or receiving communication signals. The communication interface 118 can include hardware components and/or software components implementing a particular communication protocol suitable for transporting signals over the communication link 120 to the host 130. The communication interface 118 can be referred to as a communication device or a communication interface module.

The communication link 120 may be any suitable communication link. For example, the communication link 120 may be a wired link, such as a universal serial bus (USB) link or an Ethernet link. Alternatively, the communication link 120 may be a wireless link, such as an ultra-wideband (UWB) link, an Institute of Electrical and Electronics Engineers (IEEE) 802.11 WiFi link, or a Bluetooth link.

At the host 130, the communication interface 136 may receive the image signals. The communication interface 136 may be substantially similar to the communication interface 118. The host 130 may be any suitable computing and display device, such as a workstation, a personal computer (PC), a laptop, a tablet, or a mobile phone.

The processor 134 is coupled to the communication interface 136. The processor 134 may also be described as a processor circuit, which can include other components in communication with the processor 134, such as the memory 138, the communication interface 136, and/or other suitable components. The processor 134 may be implemented as a combination of software components and hardware components. The processor 134 may include a central processing unit (CPU), a graphics processing unit (GPU), a digital signal processor (DSP), an application-specific integrated circuit (ASIC), a controller, a Field-Programmable Gate Array (FPGA) device, another hardware device, a firmware device, or any combination thereof configured to perform the operations described herein. The processor 134 may also be implemented as a combination of computing devices, e.g., a combination of a DSP and a microprocessor, a plurality of microprocessors, one or more microprocessors in conjunction with a DSP core, or any other such configuration. The processor 134 can be configured to generate image data from the image signals received from the probe 110. The processor 134 can apply advanced signal processing and/or image processing techniques to the image signals. In some aspects, the processor 134 can form a three-dimensional (3D) volume image from the image data. In some aspects, the processor 134 can perform real-time processing on the image data to provide a streaming video of ultrasound images of the object 105. In some aspects, the host 130 includes a beamformer. For example, the processor 134 can be part of and/or otherwise in communication with such a beamformer. The beamformer in the in the host 130 can be a system beamformer or a main beamformer (providing one or more subsequent stages of beamforming), while the beamformer 114 is a probe beamformer or microbeamformer (providing one or more initial stages of beamforming).

The memory 138 is coupled to the processor 134. The memory 138 may be any suitable storage device, such as a cache memory (e.g., a cache memory of the processor 134), random access memory (RAM), magnetoresistive RAM (MRAM), read-only memory (ROM), programmable read-only memory (PROM), erasable programmable read only memory (EPROM), electrically erasable programmable read only memory (EEPROM), flash memory, solid state memory device, hard disk drives, solid state drives, other forms of volatile and non-volatile memory, or a combination of different types of memory.

The memory 138 can be configured to store subject information, measurements, data, or files relating to a subject's medical history, history of procedures performed, anatomical or biological features, characteristics, or medical conditions associated with a subject, computer readable instructions, such as code, software, or other application, as well as any other suitable information or data. The memory 138 may be located within the host 130. Subject information may include measurements, data, files, other forms of medical history, such as but not limited to ultrasound images, ultrasound videos, and/or any imaging information relating to the subject's anatomy. The subject information may include parameters related to an imaging procedure such as an anatomical scan window, a probe orientation, and/or the subject position during an imaging procedure. The memory 138 can also be configured to store information related to the training and implementation of deep learning networks (e.g., neural networks) and/or information related to implementing image recognition algorithms for detecting/segmenting anatomy, image quantification algorithms, and/or image acquisition guidance algorithms, including those described herein.

The display 132 is coupled to the processor circuit 134. The display 132 may be a monitor or any suitable display. The display 132 is configured to display the ultrasound images, image videos, and/or any imaging information of the object 105.

The system 100 may be used to assist a sonographer in performing an ultrasound scan. The scan may be performed in a at a point-of-care setting. In some instances, the host 130 is a console or movable cart. In some instances, the host 130 may be a mobile device, such as a tablet, a mobile phone, or portable computer. During an imaging procedure, the ultrasound system can acquire an ultrasound image of a particular region of interest within a subject's anatomy. The ultrasound system 100 may then analyze the ultrasound image to identify various parameters associated with the acquisition of the image such as the scan window, the probe orientation, the subject position, and/or other parameters. The system 100 may then store the image and these associated parameters in the memory 138. At a subsequent imaging procedure, the system 100 may retrieve the previously acquired ultrasound image and associated parameters for display to a user which may be used to guide the user of the system 100 to use the same or similar parameters in the subsequent imaging procedure, as will be described in more detail hereafter.

The processor 134 may utilize deep learning-based prediction networks to identify parameters of an ultrasound image, including an anatomical scan window, probe orientation, subject position, and/or other parameters. The processor 134 may receive metrics or perform various calculations relating to the region of interest imaged or the subject's physiological state during an imaging procedure. These metrics and/or calculations may also be displayed to the sonographer or other user via the display 132.

Figure 2:
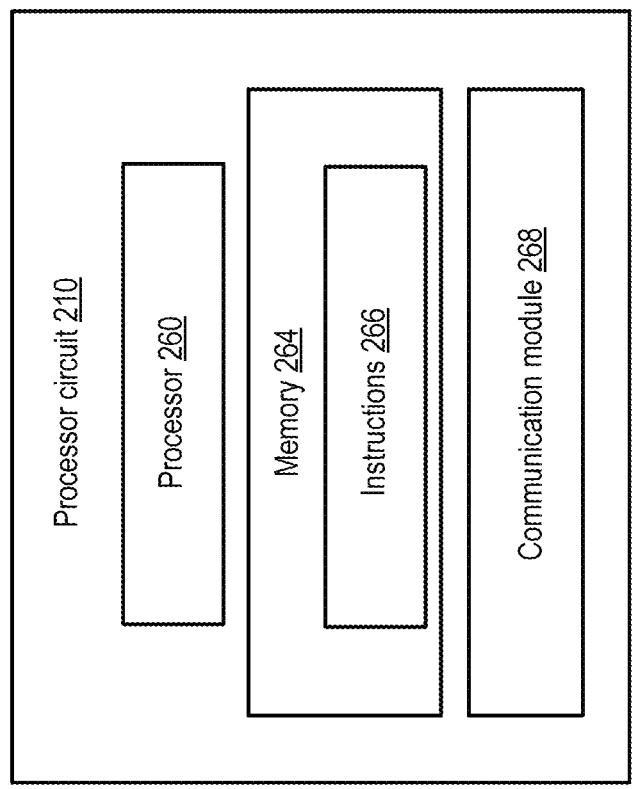
FIG. 2 is a schematic diagram of a processor circuit, according to aspects of the present disclosure.

FIG. 2 is a schematic diagram of a processor circuit, according to aspects of the present disclosure. One or more processor circuits can be configured to carry out the operations described herein. The processor circuit 210 may be implemented in the probe 110, the host system 130 of FIG. 1, or any other suitable location. For example, the processor 116 of the probe 110 can be part of the processor circuit 210. For example, the processor 134 and/or the memory 138 can be part of the processor circuit 210. In an example, the processor circuit 210 may be in communication with the transducer array 112, beamformer 114, communication interface 122, communication interface 136, and/or the display 132, as well as any other suitable component or circuit within ultrasound system 100. As shown, the processor circuit 210 may include a processor 260, a memory 264, and a communication module 268. These elements may be in direct or indirect communication with each other, for example via one or more buses.

The processor 260 may include a CPU, a GPU, a DSP, an application-specific integrated circuit (ASIC), a controller, an FPGA, another hardware device, a firmware device, or any combination thereof configured to perform the operations described herein. The processor 260 may also be implemented as a combination of computing devices, e.g., a combination of a DSP and a microprocessor, a plurality of microprocessors, one or more microprocessors in conjunction with a DSP core, or any other such configuration. The processor 260 may also include an analysis module as will be discussed in more detail hereafter. The analysis module may implement various deep learning networks and may be a hardware or a software implementation. The processor 260 may additionally include a preprocessor in either hardware or software implementation. The processor 260 may execute various instructions, including instructions stored on a non-transitory computer readable medium, such as the memory 264.

The memory 264 may include a cache memory (e.g., a cache memory of the processor 260), random access memory (RAM), magnetoresistive RAM (MRAM), read-only memory (ROM), programmable read-only memory (PROM), erasable programmable read only memory (EPROM), electrically erasable programmable read only memory (EEPROM), flash memory, solid state memory device, hard disk drives, other forms of volatile and non-volatile memory, or a combination of different types of memory. In some instances, the memory 264 includes a non-transitory computer-readable medium. The memory 264 may store instructions 266. The instructions 266 may include instructions that, when executed by the processor 260, cause the processor 260 to perform the operations described herein with reference to the probe 110 and/or the host 130 (FIG. 1). Instructions 266 may also be referred to as code. The terms "instructions" and "code" should be interpreted broadly to include any type of computer-readable statement(s). For example, the terms "instructions" and "code" may refer to one or more programs, routines, subroutines, functions, procedures, etc. "Instructions" and "code" may include a single computer-readable statement or many computer-readable statements. Instructions 266 may include various aspects of a preprocessor, deep learning network, convolutional neural network (CNN) or various other instructions or code. In some aspect, the memory 264 may be or include a non-transitory computer readable medium.

Software enabling a processor to implement a method according to the invention may be sold as a computer program product that may be a medium (e.g. a CD-ROM) comprising the software. Alternatively, the computer program product may be software that is downloadable from a server, e.g. via the internet.

The communication module 268 can include any electronic circuitry and/or logic circuitry to facilitate direct or indirect communication of data between the processor circuit 210, the probe 110, and/or the host 130. In that regard, the communication module 268 can be an input/output (I/O) device. In some instances, the communication module 268 facilitates direct or indirect communication between various elements of the processor circuit 210 and/or the probe 110 (FIG. 1) and/or the host 130 (FIG. 1).

Figure 3:
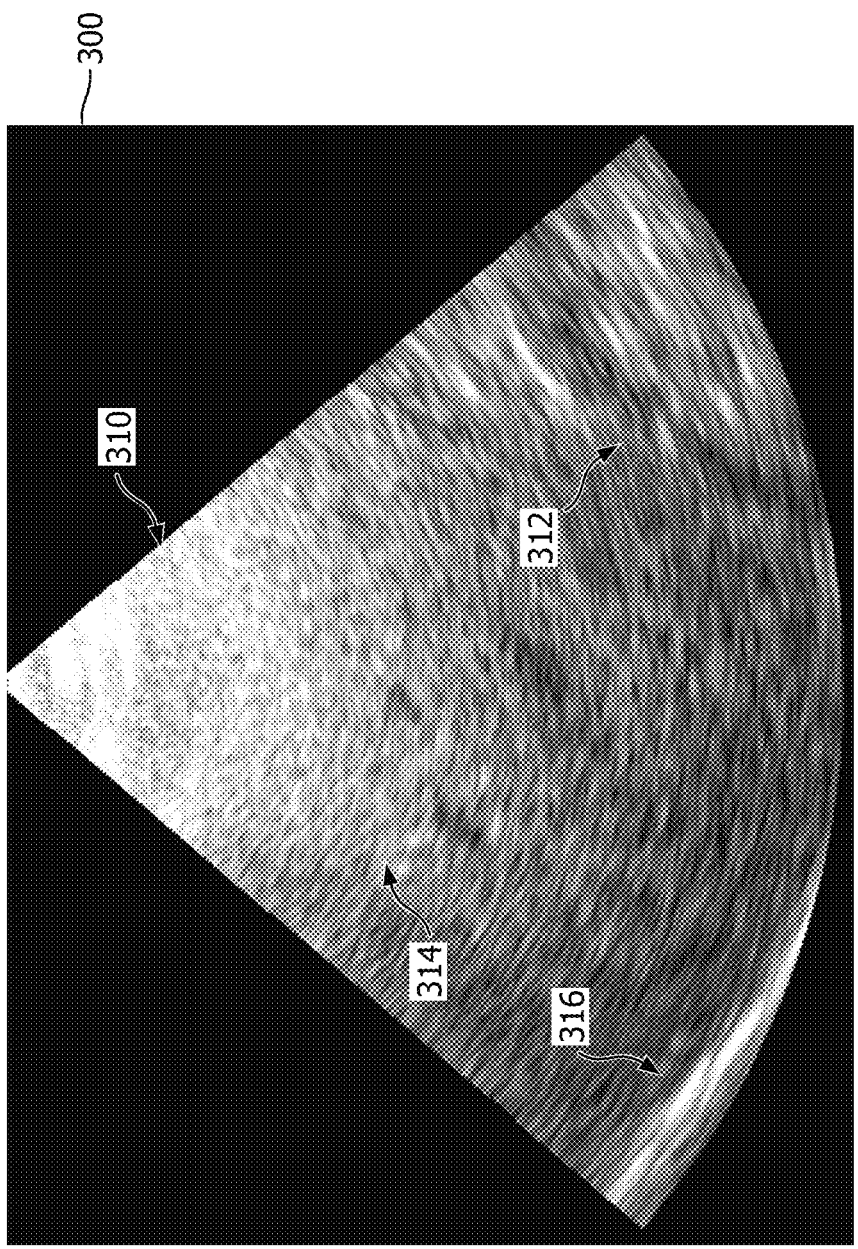
FIG. 3 is a diagrammatic view of an ultrasound image obtained with an improper depth setting, according to aspects of the present disclosure.

FIG. 3 is a diagrammatic view of an ultrasound image 310 obtained with an improper depth setting, according to aspects of the present disclosure. As shown in FIG. 3, the ultrasound image 310 may be a portion of a graphical user interface 300. It is noted that the image 310 may be an ultrasound image of any suitable portion of the subject anatomy.

In the example shown in FIG. 3, the image 310 may be an ultrasound image displaying a view of the subject anatomy including a liver 314, a kidney 312, and a diaphragm 316. In some scenarios, a sonographer may need to obtain an ultrasound image which fully depicts the liver 314, the kidney 312, and/or the diaphragm 316. In other examples, the ultrasound image may need to contain any other anatomical features of the subject. The anatomical features to be displayed within an ultrasound image, such as the image 310 may depend at least on the condition of the subject, circumstances of the ultrasound imaging procedure, or any other factors. In the example shown in FIG. 3, the ultrasound image 310 may display only a partial view of the diaphragm 316. The ultrasound image 310 may also display only a partial view of the kidney 312. The ultrasound image 310 may include full displays or partial displays of other anatomical features, such as the liver 314. In some examples, the ultrasound image 310 may display a partial view of the diaphragm 316 because the image 310 was obtained with an improper depth setting. In order to remedy the issue, the depth setting may be adjusted. As previously described, ultrasound images, such as the image 310, may be obtained with improper depth settings, or other improper settings, due to inexperience of the user of the ultrasound system, constraints on the imaging procedure, such as emergency care situations, or due to any other factors. Aspects of the present disclosure describe methods for automatically adjusting ultrasound imaging settings, such as the depth setting, to assist users in obtaining ultrasound images of higher quality leading to more accurate diagnosis and or measurements.

Figure 4:
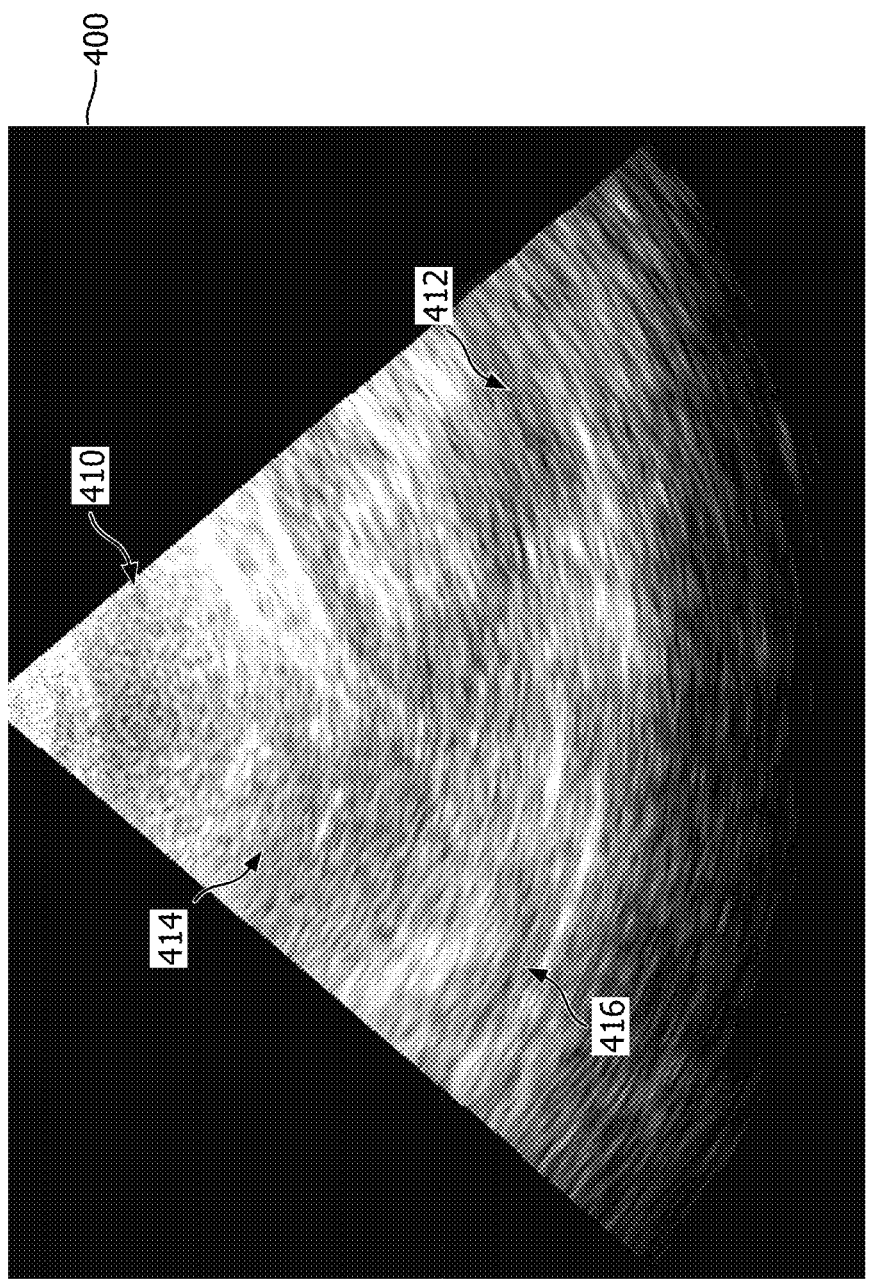
FIG. 4 is a diagrammatic view of an ultrasound image obtained with an improper gain setting, according to aspects of the present disclosure.

FIG. 4 is a diagrammatic view of an ultrasound image 410 obtained with an improper gain setting, according to aspects of the present disclosure. The ultrasound image 410 may be a portion of a graphical user interface 400. As stated with reference to the image 310 of FIG. 3, the image 410 may be an ultrasound image of any suitable portion of the subject anatomy.

The image 410 may be an ultrasound image displaying a view of the subject anatomy including the kidney 312, the diaphragm 316, and a spleen 414. In the example shown in FIG. 4, the ultrasound image 410 may display a view of the subject anatomy with a gain setting that is too high. A gain setting being too high may correspond to an oversaturation of an image. Such an oversaturation may be exemplified in the image 410. When an image is over saturated, such as the image 410, it may be more difficult for a user or a processor circuit of the ultrasound imaging system to identify anatomical features within the image. To remedy the issue, the gain setting may be adjusted. In the case shown in FIG. 4, the gain setting may be decreased. Ultrasound images may be obtained with improper gain settings due to any of the factors described with reference to FIG. 3.

Figure 5:
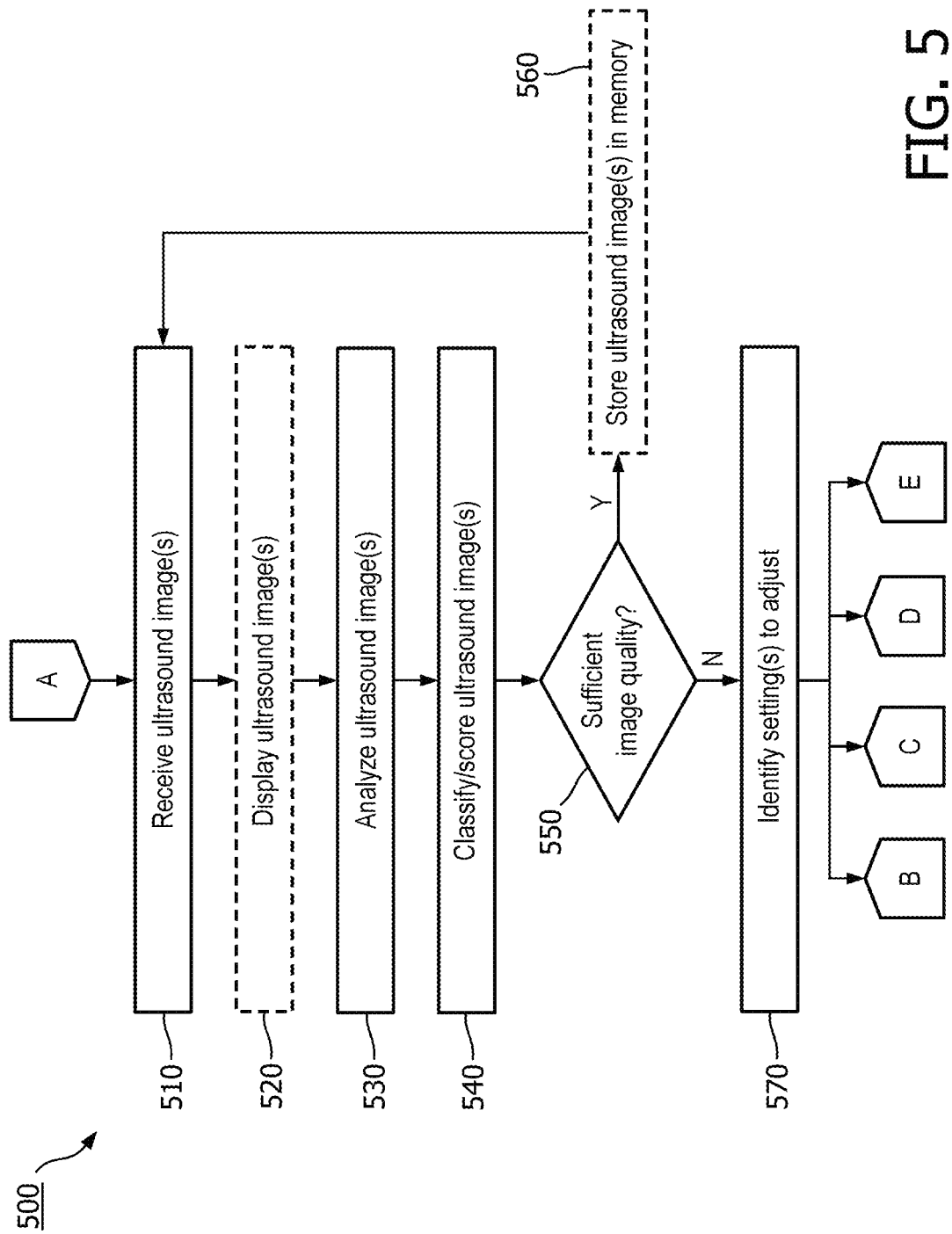
FIG. 5 is a flow diagram of a method of automatically assigning an image quality score to an ultrasound image, according to aspects of the present disclosure.

FIG. 5 is a flow diagram of a method 500 of automatically assigning an image quality score to an ultrasound image, according to aspects of the present disclosure. As illustrated, the method 500 includes a number of enumerated steps, but aspects of the method 500 may include additional steps before, after, or in between the enumerated steps. One or more of the enumerated steps may be omitted, performed in a different order, or performed concurrently. The steps of the method 500 can be carried out by any suitable component within the system 100 and all steps need not be carried out by the same component. In some aspects, one or more steps of the method 500 can be performed by, or at the direction of, a processor circuit, including, e.g., the processor 116 (FIG. 1), the processor 134 (FIG. 1), the processor 260 (FIG. 2) or any other suitable component.

Aspects of the method 500 may include classifying or scoring features of an ultrasound image and identifying corresponding ultrasound system control settings in ultrasound imaging devices to adjust in order to automatically improve the image quality of ultrasound images.

At step 510, the method 500 includes receiving one or more ultrasound image(s). As described with reference to FIG. 1, the ultrasound image(s) received at step 510 may be obtained by the ultrasound probe 110. The ultrasound images received at step 510 may then be transmitted to the processor of the ultrasound imaging system (e.g., the processor 134 of FIG. 1 and/or the processor 210 of FIG. 2).

It is noted that at step 510, the ultrasound image(s) received may include one ultrasound image or multiple ultrasound images. Specifically, in some examples, the processor circuit 210 may be configured to perform the steps 520-570 in response to receiving a single ultrasound image. In other examples, the processor circuit may receive multiple ultrasound images. For example, the processor circuit may receive multiple ultrasounds images in succession without performing the steps 520-570. In some examples, including in a live imaging scenario, the processor circuit may perform the step 520, of displaying an ultrasound image after receiving the ultrasound image, before reverting to step 510, to receive an additional ultrasound image. In some examples, the processor circuit may be configured to perform the steps 520-570 of the method 500 after receiving a set number of ultrasound images or after a set amount of time. In such cases, the steps of the method 500 may be performed with respect to one, some, or all of the ultrasound images within the predetermined number of images or length of time. For simplicity's sake, the subsequent steps of the method 500 will be described with reference to a single ultrasound image. However, it is understood that any of the steps described herein may equally apply to multiple ultrasound images.

At step 520, the method 500 includes displaying the ultrasound image received. As shown by the dotted outline of the step 520, the step 520 may be an optional step of the method 500. In some examples, the ultrasound image may be displayed by the display 132 of FIG. 1. The display of the ultrasound images at step 520 may be performed directly after the ultrasound image is received at step 510 or may occur at a later time. As described with reference to step 510, receiving an ultrasound image at step 510 and displaying the image at step 520 may correspond to a live imaging procedure.

At step 530, the method 500 includes analyzing the ultrasound image. Analyzing the ultrasound image at step 530 may include automatically identifying anatomical features within the ultrasound image. For example, the processor circuit 210 (FIG. 2) of the ultrasound system may be configured to identify any suitable anatomical features of the subject within the received ultrasound images. The processor circuit 210 may identify anatomical features within the ultrasound image according to any suitable method. For example, the processor circuit 210 may be configured to implement an image processing method, a machine learning method, or any other method or technique to automatically identify and uncle features within the ultrasound images. In some embodiments, the processor circuit 210 may use various image processing techniques to identify any anatomical features within the received ultrasound image. For example, the processor circuit 210 may use an edge-detection technique. In other embodiments, the circuit 210 may employ other image processing techniques such as pixel-by-pixel analysis to determine transitions between light pixels and dark pixels, filtering, or any other suitable techniques.

Figure 6:
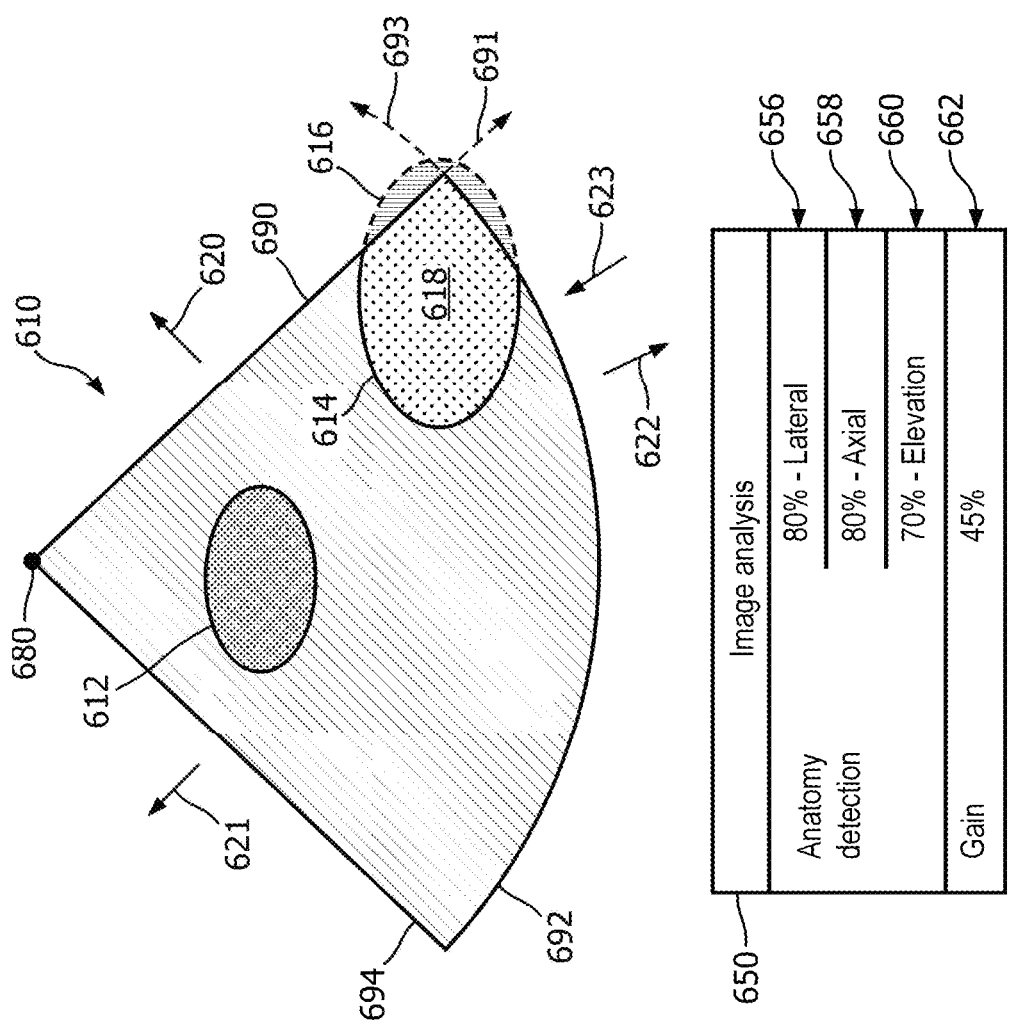
FIG. 6 is a diagrammatic view of an ultrasound image with automatically calculated measurements, according to aspects of the present disclosure.

Aspects of the step 530 of the method 500 will be described with reference to FIG. 6. FIG. 6 is a diagrammatic view of an ultrasound image with automatically calculated measurements, according to aspects of the present disclosure. As shown, FIG. 6 includes a depiction of an ultrasound image 610. The image 610 may include a view of an anatomical feature 612 and an anatomical feature 614. Displayed next to the ultrasound image 610 is a table 650 containing data related to the analysis of the image 610.

At step 530, the processor circuit 210 may analyze the image 610. In doing so, the processor circuit may be configured to determine the extent to which an expected or identified anatomical feature is present within the image 610 (e.g., measurements of the image). In some embodiments, the processor circuit may receive as an input, or otherwise determine, which anatomical features are expected to be present within the image 610. For example, during a particular type of imaging procedure, the sonographer may need to see complete views of the liver, the kidney, and diaphragm. The sonographer may input these anatomical features to the ultrasound system. This input may include identifications of the anatomical features or may include a selection of a preconfigured type of imaging procedure. In other embodiments, the processor circuit may not have access to data corresponding to expected anatomical features, but may only identify anatomical features within received images, as described.

For each identified anatomical feature within the image 610, the processor circuit may determine the extent to which the anatomical feature is visible within the image. For example, the table 650 may correspond to the anatomical feature 614 of the image 610. At step 530, the processor circuit may identify that a portion 618 of the anatomical feature 614 is observed within the image 610 and that a portion 616 of the anatomical feature 614 is not observed.

In the example shown in FIG. 6, the anatomical feature 614 may be cut off in a number of directions. For example, the anatomical feature 614 may be cut off in a lateral direction, an axial direction, and an elevational direction. The lateral direction may be shown by the arrows 620 and 621 and may correspond to a direction around an origin 680 of the image 610. Specifically, the lateral direction shown by the arrow 620 may correspond to a counterclockwise direction about the origin 680. The lateral direction shown by the arrow 621 may correspond to a clockwise direction about the origin 680. The axial direction may be shown by the arrows 622 and 623 and may correspond to a direction away from and toward the origin 680. An elevational direction may correspond a direction orthogonal to both the lateral and axial direction and may be characterized as extending into and out of the page of FIG. 6.

As shown in FIG. 6, the anatomical feature may be cut off in all three of the directions just described. The processor circuit 210 of the ultrasound imaging system may estimate the extent of presence of the anatomical feature 614 in any or all of these directions. For example, to determine the extent of presence of the anatomical feature 614 in the lateral direction (i.e., lateral presence 656) the processor circuit may identify which image border of the image 610 cuts off the anatomical feature 614. In the example shown, the image border 690 cuts off the anatomical feature 614 in a lateral direction. For illustration purposes, a border 691 is shown extending past the image border 692 in an axial direction. The processor circuit may be configured to estimate the shape and size of the portion 616 of the anatomical feature 614 because the portion 616 is not pictured within the image 610. This estimation may be based on a database of similar images of the same anatomical feature 614 within other subjects or any other data. To estimate the lateral presence 656, the processor circuit 210 may compare the regions of the anatomical feature 614 on the side of the image border 690/border 691 in the direction 621 to the regions of the anatomical feature 614 on the side of the image border 690/border 691 in the direction 620. This comparison may result in a measurement of the lateral presence 656 as shown in the table 650. The lateral presence 656 may be measured or displayed in any suitable form. For example, the lateral presence 656 may be measured or displayed as a percentage, as shown in FIG. 6. This percentage may correspond to a percentage of the anatomical feature 614 on the side of the image border 690 in the direction 621. In some examples, the lateral presence 656 may be measured or displayed as a numerical value, a ratio, an area, or by any other means.

It is noted that any or all of the lateral presence measurement 656, axial presence measurement 658, and/or the elevational presence measurement 660 or similar measurements described herein may be referred to as completeness of view measurements and may refer to the extent to which all regions of an anatomical feature are visible within an ultrasound image.

Similarly, the processor circuit may calculate an axial presence 658 of the anatomical feature 614. To determine the axial presence 658, the processor circuit may identify the image border 692, or the border farthest from the origin 680 of the image 610. This border 692 may cut off the anatomical feature 614, as it does in FIG. 6. For illustration purposes, a border 693 is shown extending past the image border 690 in the direction 620. To estimate the axial presence 658, the processor circuit 210 may compare the regions of the anatomical feature 614 on the side of the image border 692/border 693 in the direction 623 to the regions of the anatomical feature 614 on the side of the image border 692/border 693 in the direction 622 resulting in a similar percentage or other value, as shown.

The processor circuit may additionally calculate an elevational presence 660 of the anatomical feature 614. To determine the elevational presence 660 of the anatomical feature 614, the processor circuit may be configured to recognize characteristics or aspects of the anatomical feature 614 as displayed within the image 610 to determine whether the elevational plane, also referred to as the 3D plane, of the ultrasound imaging probe corresponds to an ideal cross-section of the anatomical feature 614. For example, the processor circuit may determine an observed size of the anatomical feature 614 (e.g., a cross-sectional area). The observed size may then be compared to an expected size, based on past subject data from the same subject or different subjects. In some examples, the processor circuit may additionally or alternatively calculate a measurement of elevational presence 660 of the anatomical feature 614 based on the relative size of the anatomical feature 614 to other features within the image, such as the anatomical feature 612.

In some examples, the processor circuit may additionally perform a measurement of the gain corresponding to the image 610. The gain measurement may be based on any suitable factors, including but not limited to, an observed overall brightness, saturation, and/or visibility of the image 610 and/or individual features within the image. As previously mentioned, a gain setting which is too high or too low may lead to oversaturation of the image making accurate identification of anatomical features more difficult. The measured gain 662 may be calculated in any suitable way. For example, the processor circuit may calculate the measured gain as a percentage as shown, wherein 100% corresponds to a completely saturated image. The gain measurement 662 may also be displayed as "oversaturated," "undersaturated," or "sufficient," as well as by any other suitable terms. The measured gain may also be calculated and displayed in any other way, such as a numerical value, a ratio, or by any other means. The measured gain may be determined by comparing aspects of the image 610 to other ultrasound images of the same subject, same region, or different subjects or different regions, including subjects of similar or different build or anatomical features.

Referring back to FIG. 5, at step 540, the method 500 includes classifying and/or scoring the received ultrasound images. The processor circuit may be configured to classify or score the ultrasound image in any suitable way. The processor circuit may classify the image as having a sufficient or insufficient image quality. The processor circuit may determine/assign a classification associated with each measured image aspect described with reference to FIG. 6. The processor circuit may classify ultrasound images by sufficient lateral presence, axial presence, or elevational presence of one or more of the anatomical features displayed in the image. The processor circuit may also classify the ultrasound image based on sufficient or insufficient gain.

The processor circuit may additionally or alternatively assign one or more scores to the ultrasound image. For example, the circuit may determine one or more scores based on the measurements described with reference to FIG. 6.

The processor circuit may assign a single image quality score to the ultrasound image according to the measurements described with reference to FIG. 6. A single image quality score based on the multiple measurements of FIG. 6 may be determined in any suitable way. For example, one or more measurements may be weighted more than others. Referring again to FIG. 6, in one example, the processor circuit may weigh the lateral presence and/or axial presence of an anatomical feature more heavily than the elevational presence or gain, or may weigh any of these measurements in any other way. A single image quality score of the image may be of any suitable type, including, for example, a numerical value, such as a value between a maximum and a minimum value, a percentage, a ratio, or letter ranking, a designation of a category, or by any other way.

In some examples, the processor circuit 210 may assign a score or classification to each measurement described with reference to FIG. 6. For example, the processor circuit may be configured to assign a score to the lateral presence measurement 656, a separate score to the axial presence measurement 658, another score to the elevational presence measurement 660, and another score to the gain measurement 662.

Figure 7:
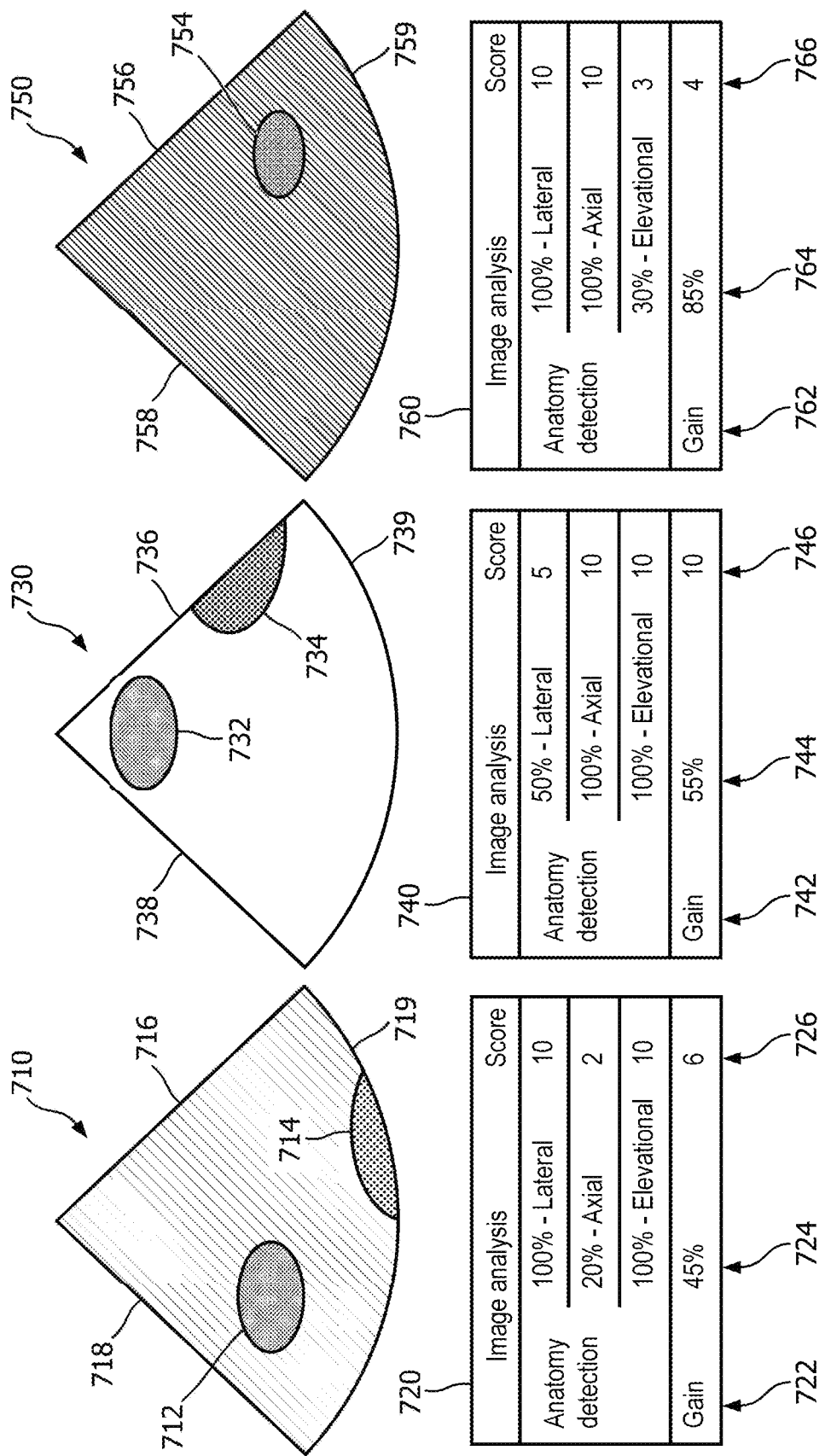
FIG. 7 is a diagrammatic view of different ultrasound images and respective measurements and scores, according to aspects of the present disclosure.

Referring now to FIG. 7, exemplary ultrasound images are provided with corresponding measurements and scores. FIG. 7 is a diagrammatic view of different ultrasound images and respective measurements and scores, according to aspects of the present disclosure. FIG. 7 may illustrate one way in which the processor circuit 210 may assign a score to any of the measurements of an ultrasound image.

For example, in FIG. 7, an ultrasound image 710 is provided. The ultrasound image 710 may include a depiction of an anatomical feature 712 and an anatomical feature 714. As explained with reference to FIG. 6, the processor circuit 210 may analyze the image 710 to determine one or more measurements associated with the image 710. These measurements are displayed in table 720 corresponding to the image 710. As an example, the measurements in the table 720 may correspond to the anatomical feature 714 of the image 710. The table 720 includes measurement categories 722 and corresponding measurements 724. For example, the measurements 724 may include a lateral presence measurement, an axial presence measurement, an elevational presence measurement, and a gain measurement. In the example shown by the table 720 and the image 710, the processor circuit may determine that the lateral presence of the anatomical feature 714 is 100%. This determination may be based on the fact that the anatomical feature 714 is not cut off in a lateral direction. In other words, the anatomical feature 714 is not cut off by either of the image borders 716 or 718. The processor circuit may determine that the axial presence measurement is 20%. This determination may be based on the fact that the anatomical feature 714 is cut off in an axial direction or that the anatomical feature is cut off by the image border 719. The processor circuit may determine that the elevational presence measurement is 100%. This determination may be based on an estimation made by the processor circuit that the elevational plane or 3D plane used to obtain the image 710 is optimal with respect to the anatomical feature 714. As previously explained, this may be based on the size, including the relative size, of the anatomical feature 714 with respect to any other features of the image 710. The processor circuit 210 may additionally determine that the gain measurement of the image 710 is 45%. In some embodiments, the processor circuit may determine that the gain measurement of the image 710 is undersaturated. This undersaturation may be illustrated by the shading of the image 710. An undersaturated image may make it difficult for a user or a processor circuit to identify features of the image 710 according to an image analysis algorithm. Alternatively, the processor circuit may assign a score as an indication of the image 710 being undersaturated in any other way.

As shown in FIG. 7 with reference to the table 720, the processor circuit may be configured to determine a score 726 associated with each of the measurements 724. The scores 726 associated with the measurements 724 may be determined in any way and may be of any suitable format. For example, the scores 726 shown in the table 720 of FIG. 7 may correspond to a range of values between 0 and 10. For example, an optimal measurement 724 may correspond to a score of 10. Less than optimal measurements may similarly correspond to values less than 10. The association between the measurements 724 and the scores 726, however, may be established in any other way. For example, the score 726 may be any other value within any other range, may be a percentage, a category, a letter, or any other format for conveying a level of sufficiency of the measurements 724.

As shown in FIG. 7, the lateral presence measurement of 100% may correspond to a lateral presence score of 10. The axial presence measurement of 20% may correspond to an axial presence score of 2. The elevational presence measurement of 100% may correspond to an elevational presence measurement of 10. The gain measurement of 45% may correspond to a score of 6. In some embodiments, an optimal gain measurement may not be 100%, but may be some different percentage or value different. In the example shown in image 710 and the corresponding table 720, a gain measurement of 45% may correspond to a desaturated image or a gain setting that is too low for optimal image quality. The score of 6, being less than the optimal score of 10, may therefore illustrate the deficiency in the gain setting.

In FIG. 7, an additional ultrasound image 730 is provided. The ultrasound image 730 includes a depiction of an anatomical feature 732 and an anatomical feature 734. The processor circuit 210 may analyze the image 730 to determine one or more measurements associated with the image 730, these measurements displayed in table 740. The measurements in the table 740 may correspond to the anatomical feature 734. The table 740 includes measurement categories 742 and corresponding measurements 744. In the example shown by the table 740 and the image 730, the processor circuit may determine that the lateral presence of the anatomical feature 734 is 50%. This determination may be based on the fact that the anatomical feature 734 is cut off in a lateral direction. As shown in the image 730, the anatomical feature 734 is cut off by the image border 736. The processor circuit may determine that the axial presence measurement is 100%. This determination may be based on the fact that the anatomical feature 734 is not cut off in an axial direction by the image border 739. The processor circuit may determine that the elevational presence measurement is 100% similar to the measurements 724 of the table 720 described previously. The gain measurement of the image 730 may be 55%. In some embodiments, the processor circuit may determine that the gain measurement of the image 710 is properly saturated or that the gain setting is optimal.

The processor circuit 210 may be configured to determine a score 746 associated with each of the measurements 744. The scores 746 may be determined according to any of the methods or principles described with reference to table 720 described previously.

As shown in the table 740, the lateral presence measurement of 50% may correspond to a lateral presence score of 5. The axial presence measurement of 100% may correspond to an axial presence score of 10. The elevational presence measurement of 100% may correspond to an elevational presence measurement of 10. The gain measurement of 55% may correspond to a score of 10.

An additional exemplary ultrasound image 750 is shown in FIG. 7. The ultrasound image 750 includes a depiction of an anatomical feature 754. The processor circuit 210 may analyze the image 750 to determine one or more measurements associated with the image 750, these measurements displayed in table 760. The measurements in the table 760 may correspond to the anatomical feature 754. The table 760 includes measurement categories 762 and corresponding measurements 764. In this example, the processor circuit may determine that the lateral presence of the anatomical feature 754 is 100%. This determination may be based on the fact that the anatomical feature 754 is not cut off in a lateral direction. As shown in the image 750, the anatomical feature 754 is not cut off by either of the image borders 756 or 758. The processor circuit may determine that the axial presence measurement is 100%. This determination may be based on the fact that the anatomical feature 754 is not cut off in an axial direction by the image border 759. The processor circuit may determine that the elevational presence measurement is 30%. In some examples, the anatomical feature 754 may be the same type of feature as the anatomical feature 714 of the image 710 and/or the anatomical feature 754 of the image 750. Based on the recognition of the type of anatomical feature of the anatomical feature 754, the processor circuit 210 may identify that the elevational plane corresponding to the image 750 or the anatomical features 754 is not optimal. This determination may be based on the size of the anatomical feature 754 compared to an expected size, such as the size of the anatomical features 714 and/or 734. In addition, the determination of the elevational plane as suboptimal may be based on the presence or lack of other expected anatomical features within the image 750, such as the anatomical features 712 and/or 732. The gain measurement of the image 730 may be 85% corresponding to an oversaturated image. This oversaturation may be illustrated by the shading of the image 750. An oversaturated image may make it difficult for a user or a processor circuit to identify features of the image 750 according to an image analysis algorithm.

The processor circuit 210 may be configured to determine a score 766 associated with each of the measurements 764. The scores 766 may be determined according to any of the methods or principles described with reference to table 720 and/or table 740 described previously.

As shown in the table 760, the lateral presence measurement of 100% may correspond to a lateral presence score of 10. The axial presence measurement of 100% may correspond to an axial presence score of 10. The elevational presence measurement of 30% may correspond to an elevational presence measurement of 3. The gain measurement of 85% may correspond to a score of 4. In some examples, the score associated with gain measurements may correspond to whether the image is undersaturated or oversaturated. For example, an image with an appropriate saturation level may correspond to a value, such as 10, with undersaturated images corresponding to scores less than 10 and oversaturated images corresponding to scores greater than 10. In such an example, the gain score of the image 750 may alternatively be a value greater than 10 to convey the oversaturation of the image 750.

The ultrasound images 710, 730, and 750 shown in FIG. 7 may be images which were analyzed by the processor circuit 210 of the imaging system 100 as described or may be images with corresponding data received by the processor circuit 210. For example, the images 710, 730, and 750 and their corresponding tables of data may be exemplary of multiple ultrasound images and corresponding data within a database accessed by the processor circuit in assigning scores and/or recommended adjustment to ultrasound system settings for a received ultrasound image. In some instances, the ultrasound images 710, 730, and 750 can be considered references images to which ultrasound images acquired during an imaging procedure are compared. In some instances, the ultrasound images 710, 730, and 750 are part of a training data set (e.g., ground truth data) that is used to train a machine learning/AI algorithm.

Figure 8:
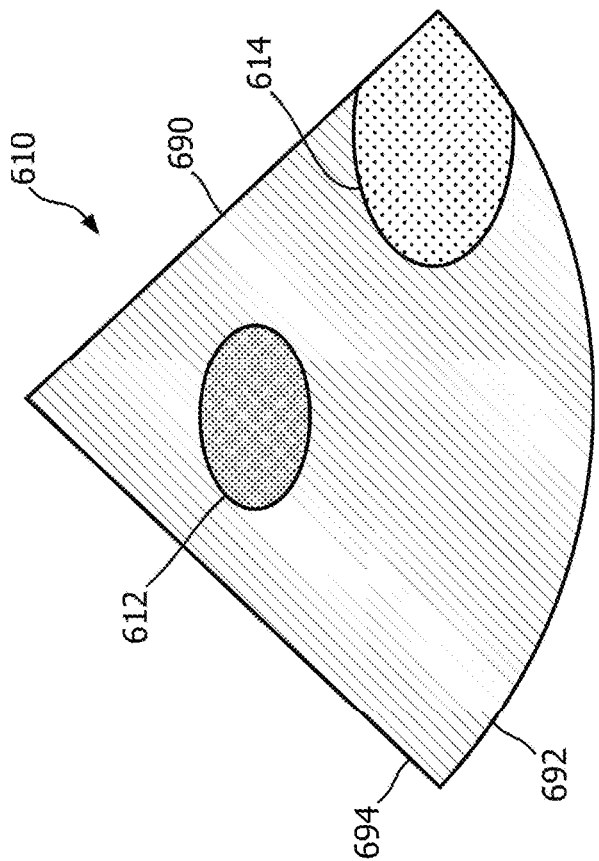
FIG. 8 is a diagrammatic view of an ultrasound image with automatically calculated measurements, scores, and setting adjustments, according to aspects of the present disclosure.

Referring now to FIG. 8, FIG. 8 is a diagrammatic view of an ultrasound image 610 with automatically calculated measurements, scores, and setting adjustments, according to aspects of the present disclosure. The table 850 shown in FIG. 8 includes measurement categories 852, measurements 854, scores 856, and recommended setting adjustments 858. The processor circuit 210 may compare features of the image 610 to any of the images within the database (e.g., the images 710, 730, and/or 750) to determine scores 856 associated with each of the measurements 854. As explained herein, the scores 856 may be determined as an output of an artificial intelligence (AI) algorithm. For example, an AI algorithm may be trained to identify various features of the image 610 based on multiple training images. In some examples, the scores 856 may be based on any other comparison of the image 610 with one or more reference images. It is noted that, in some instances, an artificial intelligence algorithm may be referred to as a machine learning algorithm and a machine learning algorithm may be referred to as an artificial intelligence algorithm.

For example, the processor circuit 210 may be configured to compare a received image (e.g., the image 610 of FIG. 6) to any of the images of the database (e.g., the images 710, 730, and/or 750). In comparing these images, the processor circuit may identify similarities between the images and assign similar scores based on the similarities. As an example, the observed gain measurement 662 of 45% of the image 610 may be similar to the gain measurement of 45% of the image 710. Based on this similarity, the processor circuit may assign a score of 6 for the gain measurement of the image 610. Similarly, the processor circuit may assign a suboptimal lateral presence score to the image 610 based on the feature 614 being cut off by the border 690 like the feature 734 of the image 730 is cut off by the border 736. Other scores may be assigned based on similar comparisons.

In some examples, the processor circuit 210 may be configured to implement and/or train a machine learning algorithm to determine any of the measurements 854, the scores 856, or the recommended setting adjustments 858. For example, the images 710, 730, and 750 of FIG. 7 may be example images of annotated images of a database of training images. For example, multiple training images may be annotated by experts in the field to identify measurements of the image, including lateral presence, axial presence, elevational presence, and saturation or gain measurements, corresponding scores, and/or recommended setting adjustments to remedy any deficiencies. An AI algorithm may then be trained to determine any of these values based on the training image set.

In an example in which the processor circuit uses a machine learning algorithm to analyze, measure, classify, and/or score a received image, the machine learning algorithm may be of any suitable type. For example, a classification process may include a random forest algorithm, a classification tree approach, a convolutional neural network (CNN) or any other type of deep learning network. In some instances, the processor circuit 210 (FIG. 2) can implement a statistical model. It is noted that the measurements 854 of table 850 and/or the scores 856 of table 850 may be determined with separate algorithms or with the same algorithm, including a classical comparison algorithm, a machine learning algorithm, or according to any other algorithm, method, or process.

The recommended setting adjustments 858 shown in the table 850 of FIG. 8 may additionally be calculated by the processor circuit 210 and may indicate how the measurements 854 may be improved to improve image quality. Additional details describing how various settings of the ultrasound imaging system may be adjusted to improve image quality will be described with reference to FIGS. 9-14.

Referring back to FIG. 5, after a received ultrasound image, such as the image 610, is analyzed and assigned a score or classification according to any of the methods described with reference to FIGS. 6-8, at the step 550, the method 500 includes determining whether the received image is of sufficient image quality. This determination may be made in any number of ways. As one example, an image quality score may be compared to a threshold image quality score. In some examples, the image quality score may be a single score corresponding to the received ultrasound image (e.g., the image 610) as a whole and may be based on any of the measurements described previously. In such an example, the processor circuit may determine that the image is of sufficient image quality when the single score satisfies the threshold score (e.g., if the single score meets, exceeds, or is less than the threshold score).

To determine whether the received image is of sufficient image quality, the processor circuit 210 may compare multiple scores to multiple thresholds. The processor circuit may compare any of the scores of the table 850 to corresponding threshold scores. The processor circuit may determine that the received image is of sufficient image quality in response to determining that each score satisfies corresponding threshold scores. In such case, if any of the scores (e.g., the scores 856 of the table 850) do not exceed a corresponding threshold, the processor circuit may determine that the received image is not of sufficient image quality. The processor circuit may determine that the received image is of sufficient image quality if a predetermined number of scores (e.g., any of the scores 856) exceed corresponding thresholds. The processor circuit may be configured to determine that the image is of sufficient image quality in response to any one or more of the scores satisfying a respective threshold. In some embodiments, any of the scores described herein may be a scalar, vector, or matrix. Similarly, the threshold score may be a scalar, vector, or matrix. The threshold score may be a multiple level score to produce binary or multi-class classification decisions.

As shown in FIG. 5, in response to the processor circuit determining that the received image is of sufficient image quality, the method 500 may progress to step 560. However, if the processor circuit determines that the image is not of sufficient image quality, the method 500 may progress to the step 570.

At the step 560, the method 500 includes storing the ultrasound image in a memory. As shown in FIG. 5, the step 560 may be an optional step. At the step 560, any suitable number of images may be stored, including only one image analyzed or additional images preceding or following the image or a set of images.

After step 560 is completed, the method 500 may revert back to the step 510 at which point an additional ultrasound image or set of ultrasound images is received and method 500 may be repeated. As shown by the progression from step 560 back to the step 510, the method 500 illustrated in FIG. 5 may describe a recursive process. For example, a recursive process may include performing each of the steps 520-550 for each received ultrasound image in a live imaging scenario. As explained, the method 500, as well as any of the methods described below with reference to FIGS. 9-12, may be performed repeatedly or iteratively with respect to each received ultrasound image. In some examples, however, the processor circuit may perform any of the steps of these same methods according to a periodic process. For example, after determining at the step 550 that the score(s) of a received ultrasound image satisfies any corresponding threshold(s) and optionally performing the step 560, the processor circuit may receive an additional ultrasound image (or multiple ultrasound images) without performing the steps 520-550 of the method 500. In this way, these additional images may be received and displayed to the user but not analyzed or assigned a score. In some examples, the number of ultrasound images received without analysis after the processor circuit determines that one ultrasound image is of sufficient quality may be a predetermined number or may correspond to a predetermined time period. For example, after one ultrasound image is considered to be of sufficient image quality at the step 550 and the method reverts to the step 510, one, two, three, ten, or more ultrasound images may be received, or any number therebetween, without analyzing these images according to the method 500. In some examples, after one ultrasound image is considered to be of sufficient image quality at the step 550 and the method reverts to the step 510, the processor circuit may receive additional images without analyzing them according to the method 500 for any suitable period of time, such as 0.5 seconds, 1 second, 2 seconds, or more, as well as any suitable time less than or between these values.

At step 570, the method 500 includes identifying a setting to adjust. Referring again to FIG. 8, any of the measurements of the received image 610 may correspond to a setting which, when adjusted, may be improve the image quality. For example, a lateral presence score below a corresponding threshold may correspond to an adjustment in a lateral angle setting of the ultrasound imaging system. An axial presence score below a corresponding threshold may correspond to an adjustment in a depth setting of the ultrasound imaging system. An elevational presence score below a corresponding threshold may correspond to an adjustment in a 3D elevational plane of the ultrasound imaging system. A gain score below a corresponding threshold may correspond to an adjustment in a gain setting of the ultrasound imaging probe.

As shown in FIG. 5, after the processor circuit identifies a setting to adjust, the method 500 may proceed to one of several setting adjustment algorithms. For example, if, at step 570, the processor circuit identifies that a depth setting should be adjusted, the method 500 may proceed to the method 900 of FIG. 9 as shown by block B. If the processor circuit identifies that a gain setting should be adjusted, the method 500 may proceed to the method 1000 of FIG. 10 as shown by block C. If the processor circuit identifies that a lateral angle setting should be adjusted, the method 500 may proceed to the method 1100 of FIG. 11 as shown by block D. If the processor circuit identifies that an elevational angle setting should be adjusted, the method 500 may proceed to the method 1200 of FIG. 12 as shown by block E.

Figure 9:
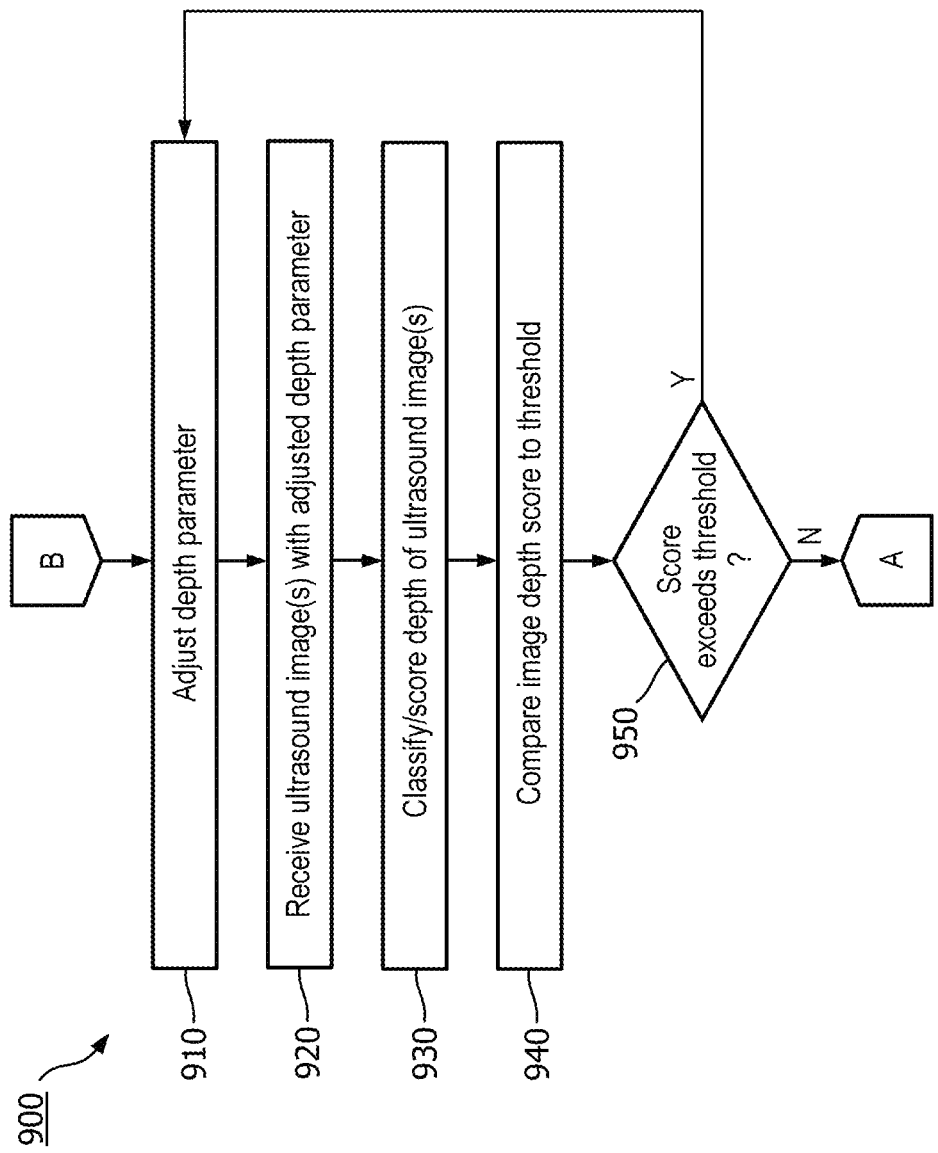
FIG. 9 is a flow diagram of a method of automatically adjusting a depth parameter, according to aspects of the present disclosure.

FIG. 9 is a flow diagram of a method of automatically adjusting a depth parameter, according to aspects of the present disclosure. As illustrated, the method 900 includes a number of enumerated steps, but aspects of the method 900 may include additional steps before, after, or in between the enumerated steps. In some aspects, one or more of the enumerated steps may be omitted, performed in a different order, or performed concurrently. The steps of the method 900 can be carried out by any suitable component within the system 100 and all steps need not be carried out by the same component. In some aspects, one or more steps of the method 900 can be performed by, or at the direction of, a processor circuit, including, e.g., the processor 116 (FIG. 1), the processor 134 (FIG. 1), the processor 260 (FIG. 2) or any other suitable component.

The method 900 may illustrate a depth adjustment algorithm for automatically adjusting a depth setting. At step 910, the method 900 includes adjusting a depth parameter. The depth adjustment algorithm described by the method 900 may include a depth selection and/or estimation algorithm, a classification algorithm, or a rule-based algorithm.

In one example, the processor circuit may be configured to estimate an optimal depth setting based on the received image, the axial presence measurements of an anatomical feature of the received image (e.g., the axial presence measurement 658), and/or the axial presence score of an anatomical feature of the received image (see e.g., FIG. 8). For instance, the processor circuit 210 may access a database including exemplary images (e.g., any of the images of FIG. 7) along with accompanying data including axial presence measurements and/or depth settings which improved the axial presence measurements and subsequent image quality of the images. Based on this information, the processor circuit 210 may implement a similar depth setting at step 910.

In other examples, the processor circuit 210 may estimate an optimal depth setting in any other way. For example, the processor circuit 210 may receive or establish a relationship between physical dimensions within a received image and increments of a depth setting. For example, the processor circuit 210 may determine or estimate a distance at an outer border of the image from the ultrasound imaging probe and may establish a relationship between an increase in the depth setting with an increase in this distance from the ultrasound imaging probe. In some examples, the processor circuit may estimate diameter, cross sectional area, circumference, or any other dimension of an anatomical feature and increase the depth setting based on the dimensions of the anatomical feature within the image. For example, the processor circuit may estimate a diameter of an anatomical feature in an axial direction. The processor circuit 210 may additionally estimate a portion of the axial diameter of the anatomical feature which is not displayed within the received image, or a portion that is cutoff by the outer image boundary in an axial direction. The processor circuit 210 may then increase the depth of the ultrasound imaging system by an amount corresponding to the portion of the axial diameter of the anatomical feature which is not displayed within the image.

In some examples, the processor circuit may not estimate a depth setting value corresponding to an increase in image quality but may determine whether the depth setting should be increased or decreased. At the step 910, the processor circuit 210 may then either increase or decrease the depth setting by incremental amounts. In some embodiments, the processor circuit may increment the depth setting by a predetermined amount. For example, a user of the system or the processor circuit 210 itself may specify extent of and incremental change in the depth setting. The amount of change of one increment may be determined based on the region of the subject anatomy imaged, the condition to be diagnosed, or any other factor. In some embodiments, the amount of change of one increment may be determined based on any of the measurements or scores of the received ultrasound image. For example, a measurement or score of an ultrasound image indicating low axial presence of an anatomical feature within an ultrasound image may correspond to a larger increment of change of the depth setting. Alternatively, an axial presence measurement or score indicating that a large portion of an anatomical feature is within the received image may correspond to a smaller incremental change of the depth setting.

At step 920, the method 900 includes receiving an ultrasound image or ultrasound images with the adjusted depth parameter. After the depth setting is adjusted as previously explained with reference to step 910, the ultrasound imaging system may acquire one or more additional ultrasound images with the new depth setting. As explained with reference to step 510 of the method 500, the received ultrasound image may include one or more ultrasound images, however for the purposes of explaining the method 900, the ultrasound image received at step 920 and described in subsequent steps will be described as a single ultrasound image.

At step 930 of the method 900, the method 900 includes classifying or scoring the depth of the ultrasound image. In some examples, step 930 may include measuring an axial presence of the anatomical feature in question in the ultrasound image received at step 920. This measurement may include any of the methods described with reference to FIGS. 6-8. The classification, measurement, and or score determined at step 930 may also share any characteristics or features to those explained with reference to FIGS. 6-8.

At step 940, the method 900 includes comparing the image depth score to a threshold score. In some examples, the processor circuit 210 may determine or receive a threshold depth score. The threshold depth score may also be referred to as an axial presence score.

At step 950, the method 900 includes determining whether the depth score satisfies the threshold score. In some embodiments, the depth score may exceed the threshold score when no regions of the anatomical feature in question are cut off by the outer axial image border (e.g., the border 692 of FIG. 6). In some embodiments, the depth score may exceed the threshold score when a certain predetermined percentage of the anatomical feature is closer axially to the origin of the ultrasound image then the outer axial image border.

It is noted that numerous variations of the algorithm outlined by the method 900 may be implemented. For example, at steps 940 and 950, the method 900 may alternatively not compare the depth score to a threshold score, but may compare the depth score to the previously depth score assigned before the depth parameters were adjusted at 910 to determine whether an improvement in the depth occurred. In response to an improvement in the depth setting observed at 930, the method may revert back to the step 910 and further adjust the depth parameter in a similar way. This process may be completed iteratively until no change or a negative change in the depth score is observed, at which point the depth parameter corresponding to the highest depth score is selected and the processor circuit reverts back to the method 500 or any other method.

If, at step 950, the processor circuit 210 determines that the score does not exceed the threshold score, the method 900 may revert back to the step 910. In this example, the depth setting is again adjusted according to any of the methods previously described. After the step 910 is completed, the remaining steps of the method 900 may be similarly completed. In this way, the processor circuit 210 may iteratively perform the method at 900 shown and described in FIG. 9 until the depth score satisfies the threshold.

If, at step 950, the processor circuit 210 determines that the score does exceed the threshold score, the method 900 may revert back to the method 500 of FIG. 5 as shown by the block A. In some embodiments, the processor circuit 210 may refer to any of the other methods, including the method 1000, 1100, and/or 1200, depending on which settings are determined by the processor circuit to be adjusted at this step 570 of the method 500 of FIG. 5.

For example, if at the step 570 of the method 500, the processor circuit determines that a depth setting as well as a gain setting should be adjusted, the processor circuit may perform the steps of the method 900 to adjust and optimize the depth setting, and may then perform the steps of the method 1000 to adjust and optimize the gain setting. In this way, after the depth score is determined to exceed its corresponding threshold at the step 950 of the method 900, the processor circuit may proceed to the method 1000 rather than back to the method 500. In a similar way, any of the algorithms described with reference to FIGS. 9-12 may be performed after the steps of the method 500 are performed.

In addition, any of the methods of FIGS. 9-12 may be performed simultaneously. In some embodiments, any of the methods of FIGS. 9-12 may also be performed independently of the method 500. For example, while the steps of the method 500 of FIG. 5 as described herein may serve to trigger any of the algorithms of FIGS. 9-12, this need not always be the case. For example, the processor circuit 210 may perform the steps of the method 900 in FIG. 9, the method 1000 of FIG. 10, the method 1100 of the FIG. 11, and/or the method 1200 of FIG. 12 automatically or in response to a user input selecting any of these algorithms or methods.

Figure 10:
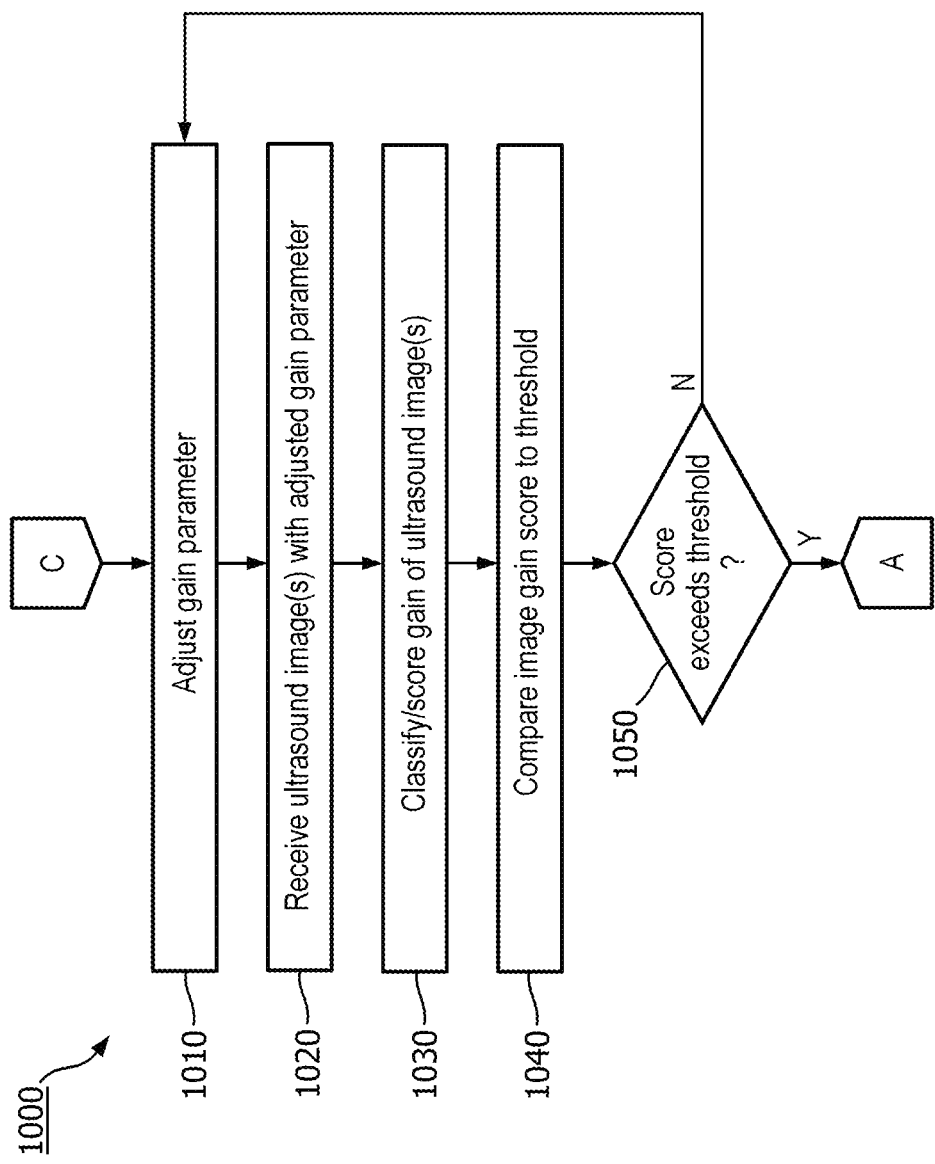
FIG. 10 is a flow diagram of a method of automatically adjusting a gain parameter, according to aspects of the present disclosure.

FIG. 10 is a flow diagram of a method of automatically adjusting a gain parameter, according to aspects of the present disclosure. As illustrated, the method 1000 includes a number of enumerated steps, but aspects of the method 1000 may include additional steps before, after, or in between the enumerated steps. One or more of the enumerated steps may be omitted, performed in a different order, or performed concurrently. The steps of the method 1000 can be carried out by any suitable component within the system 100 and all steps need not be carried out by the same component. In some aspects, one or more steps of the method 1000 can be performed by, or at the direction of, a processor circuit, including, e.g., the processor 116 (FIG. 1), the processor 134 (FIG. 1), the processor 260 (FIG. 2) or any other suitable component.

The method 1000 may illustrate a gain adjustment algorithm for automatically adjusting a gain setting. Aspects of the method 1000 may be similar to the method 900 described with reference to FIG. 9. At step 1010, the method 1000 includes adjusting a gain parameter.

In one example, the processor circuit may be configured to estimate an optimal gain setting based on the received image. To do so, the processor circuit 210 may access a database including exemplary images (e.g., any of the images of FIG. 7) along with accompanying data including observed gain measurements and corresponding gain settings including increases or decreases in gain which improved measured saturation and/or image quality. Based on this information, the processor circuit 210 may implement a similar gain setting.

In other examples, the processor circuit 210 may receive or establish a relationship between a measured level of observed saturation and increments of a gain setting. For example, the processor circuit 210 may analyze characteristics of the received image including brightness, contrast, saturation, blur, clarity, definition or any other characteristic and may establish a relationship between an increase in any of these measurements with a change in gain setting.

In some examples, the processor circuit may not estimate a gain setting value corresponding to an increase in image quality but may determine whether the gain setting should be increased or decreased. At the step 1010, the processor circuit 210 may then either increase or decrease the gain setting by incremental amounts. In some embodiments, the processor circuit may increment the gain setting by a predetermined amount, as explained with reference to method 900 of FIG. 9.

At step 1020, the method 1000 includes receiving an ultrasound image or ultrasound images with the adjusted gain parameter.

At step 1030 of the method 1000, the method 1000 includes classifying or scoring the gain of the ultrasound image. In some examples, step 1030 may include any of the measurements of image characteristics previously described.

At step 1040, the method 1000 includes comparing the image gain score to a threshold score. In some examples, the processor circuit 210 may determine or receive a threshold gain score.

At step 1050, the method 1000 includes determining whether the gain score satisfies the threshold score. If, at step 1050, the processor circuit 210 determines that the score does not exceed the threshold score, the method 1000 may revert back to the step 1010 and the process may be repeated until the gain score satisfies the threshold. If, at step 1050, the processor circuit 210 determines that the score does exceed the threshold score, the method 1000 may revert back to the method 500 of FIG. 5 as shown by the block A or any other method as previously described.

Any variations of the algorithm outlined by the method 1000 are also contemplated, including incrementally varying a gain setting and comparing it to previous gain settings until the corresponding gain score plateaus or decreases, whereupon the gain setting with the optimal gain score may be selected.

Figure 11:
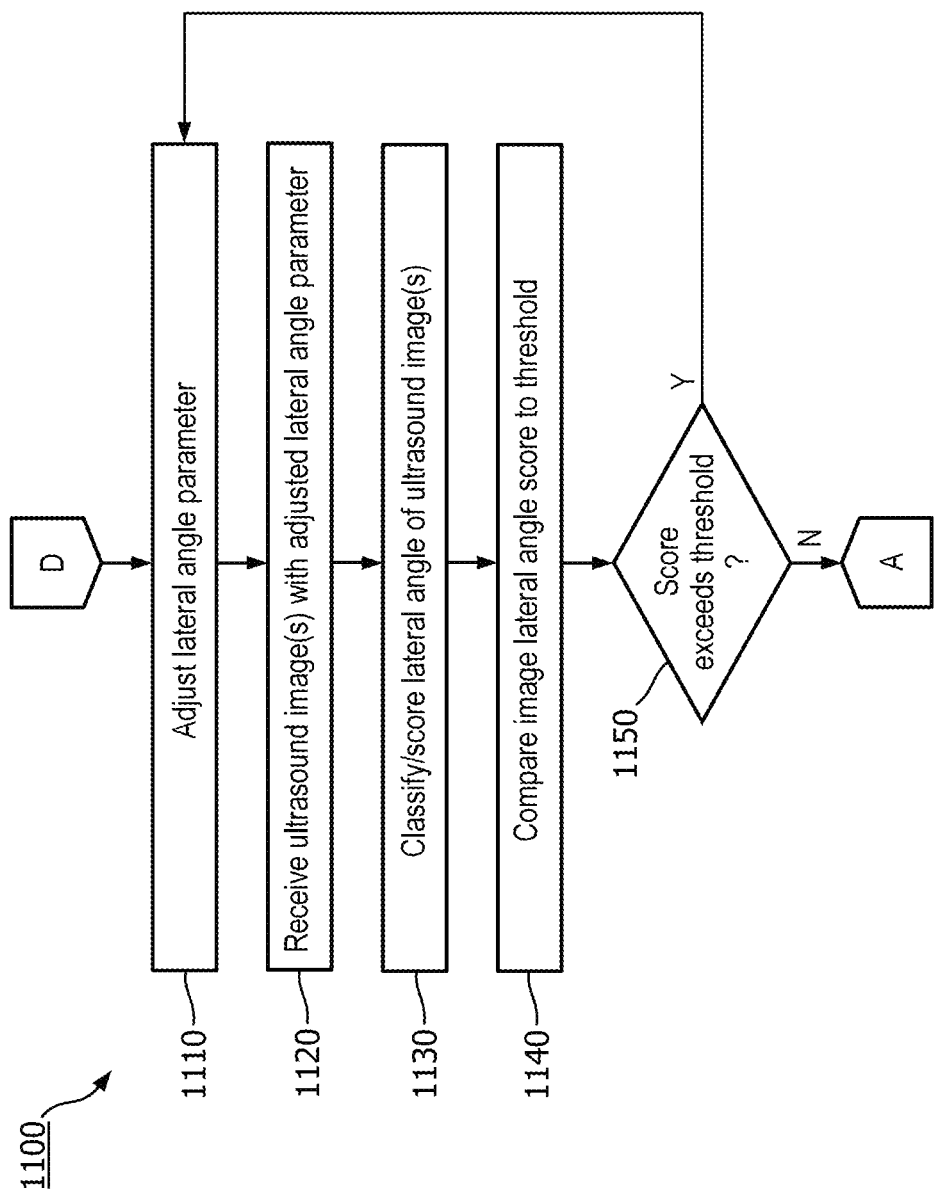
FIG. 11 is a flow diagram of a method of automatically adjusting a lateral angle parameter, according to aspects of the present disclosure.

FIG. 11 is a flow diagram of a method of automatically adjusting a lateral angle parameter, according to aspects of the present disclosure. As illustrated, the method 1100 includes a number of enumerated steps, but aspects of the method 1100 may include additional steps before, after, or in between the enumerated steps. In some aspects, one or more of the enumerated steps may be omitted, performed in a different order, or performed concurrently. The steps of the method 1100 can be carried out by any suitable component within the system 100 and all steps need not be carried out by the same component. In some aspects, one or more steps of the method 1100 can be performed by, or at the direction of, a processor circuit, including, e.g., the processor 116 (FIG. 1), the processor 134 (FIG. 1), the processor 260 (FIG. 2) or any other suitable component.

The method 1100 may illustrate a lateral angle adjustment algorithm for automatically adjusting a lateral angle setting. Aspects of the method 1100 may be similar to the method 900 and/or method 1000 described with reference to FIG. 9 and/or FIG. 10. At step 1110, the method 1100 includes adjusting a lateral angle parameter.

In one example, the processor circuit may be configured to estimate an optimal lateral angle setting based on the received image. To do so, the processor circuit 210 may access a database including exemplary images (e.g., any of the images of FIG. 7) along with accompanying data including observed lateral angles measurements and corresponding lateral angle settings including increases or decreases in the lateral angle which improved image quality. In some instances, a lateral angle setting may refer to a beam direction of an ultrasound transducer probe as well as a sector width. Based on this information, the processor circuit 210 may implement a similar lateral angle setting.

In some examples, the processor circuit may determine whether the lateral angle setting should be increased or decreased or shifted in a lateral direction. At the step 1110, the processor circuit 210 may then either increase or decrease the lateral angle setting or shift the beam in a lateral direction by incremental amounts. In some embodiments, the processor circuit may increment any of these settings by a predetermined amount, as explained with reference to method 900 and/or method 1000.

At step 1120, the method 1100 includes receiving an ultrasound image or ultrasound images with the adjusted lateral angle parameter.

At step 1130 of the method 1100, the method 1100 includes classifying or scoring the lateral angle of the ultrasound image. In some examples, step 1130 may include any of the measurements of image characteristics previously described.

At step 1140, the method 1100 includes comparing the image lateral angle score to a threshold score. In some examples, the processor circuit 210 may determine or receive a threshold lateral angle score corresponding to the extent to which the anatomical feature in question is being cut off by lateral image borders (e.g., the borders 690 and 694 of FIG. 6).

At step 1150, the method 1100 includes determining whether the lateral angle score satisfies the threshold score. If, at step 1150, the processor circuit 210 determines that the score does not exceed the threshold score, the method 1100 may revert back to the step 1110 and the process may be repeated until the lateral angle score satisfies the threshold. If, at step 1150, the processor circuit 210 determines that the score does exceed the threshold score, the method 1100 may revert back to the method 500 of FIG. 5 as shown by the block A or any other method as previously described. Like the methods previously described, any variations of the algorithm outlined by the method 1100 are also contemplated, including incrementally varying a lateral angle setting and comparing it to previous lateral angle settings until the corresponding lateral angle score plateaus or decreases, whereupon the lateral angle setting with the optimal lateral angle score may be selected.

Figure 12:
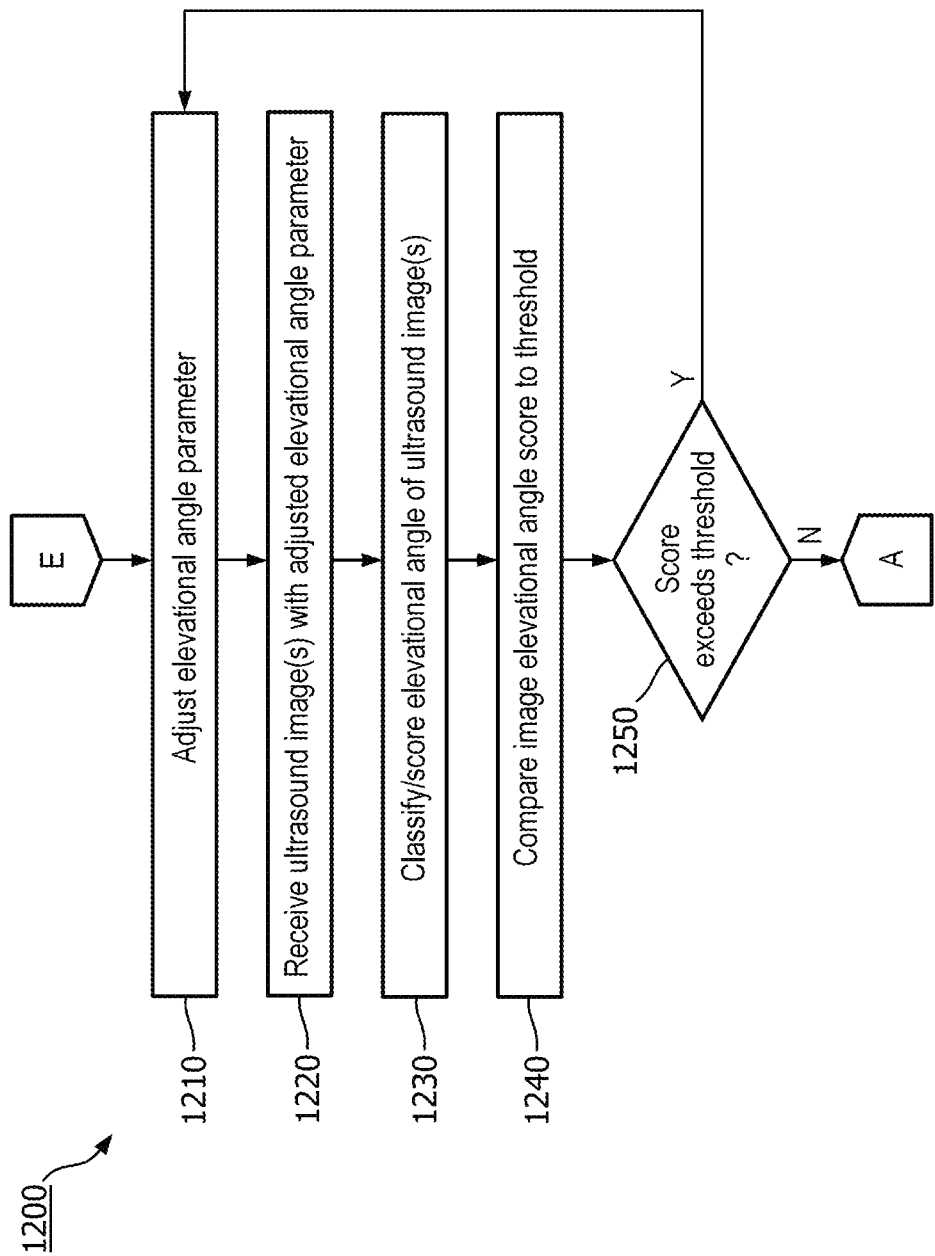
FIG. 12 is a flow diagram of a method of automatically adjusting an elevational angle parameter, according to aspects of the present disclosure.

FIG. 12 is a flow diagram of a method of automatically adjusting an elevational angle parameter, according to aspects of the present disclosure. As illustrated, the method 1200 includes a number of enumerated steps, but aspects of the method 1200 may include additional steps before, after, or in between the enumerated steps. One or more of the enumerated steps may be omitted, performed in a different order, or performed concurrently. The steps of the method 1200 can be carried out by any suitable component within the system 100 and all steps need not be carried out by the same component. In some aspects, one or more steps of the method 1200 can be performed by, or at the direction of, a processor circuit, including, e.g., the processor 116 (FIG. 1), the processor 134 (FIG. 1), the processor 260 (FIG. 2) or any other suitable component.

The method 1200 may illustrate an elevational angle adjustment algorithm for automatically adjusting an elevational angle setting. Aspects of the method 1200 may be similar to the methods 900, 1000, and/or 1100 described with reference to FIGS. 9, 10, and/or 11. In some respects, the steps of the method 1200 may apply to or be implemented by a processor circuit in connection with a 3D ultrasound probe, or probe including a matrix array. At step 1210, the method 1200 includes adjusting an elevational angle parameter.

In one example, the processor circuit may be configured to estimate an optimal elevational angle setting based on the received image. To do so, the processor circuit 210 may access a database including exemplary images (e.g., any of the images of FIG. 7) along with accompanying data including observed elevational angle measurements and corresponding elevational angle settings including increases or decreases in the elevational angle which improved measured image quality or the elevational presence of an anatomical feature within the image. Based on this information, the processor circuit 210 may implement a similar elevational angle setting.

In other examples, the processor circuit 210 may receive or establish a relationship between a measured elevational presence of an anatomical feature and increments of an elevational angle setting. For example, the processor circuit 210 may analyze characteristics of the received image including the size, shape, or other dimensions of an anatomical feature and may establish a relationship between a change in any of these measurements with a change in the elevational angle setting.

In some examples, the processor circuit may determine whether the elevational angle setting should be increased or decreased. At the step 1210, the processor circuit 210 may then either increase or decrease the elevational angle, also referred to as a 3D plane, by incremental amounts. In some embodiments, the processor circuit may increment the elevational angle by a predetermined amount, as explained with reference to previous methods.

At step 1220, the method 1200 includes receiving an ultrasound image or ultrasound images with the adjusted elevational angle.

At step 1230 of the method 1200, the method 1200 includes classifying or scoring the elevational presence or elevational angle of the ultrasound image. In some examples, step 1230 may include any of the measurements of image characteristics previously described.

At step 1240, the method 1200 includes comparing the elevational presence score to a threshold score. In some examples, the processor circuit 210 may determine or receive a threshold elevational presence or elevational angle score.

At step 1250, the method 1200 includes determining whether the elevational presence score satisfies the threshold score. If, at step 1250, the processor circuit 210 determines that the score does not exceed the threshold score, the method 1200 may revert back to the step 1210 and the process may be repeated until the score satisfies the threshold. If, at step 1250, the processor circuit 210 determines that the score does exceed the threshold score, the method 1200 may revert back to the method 500 of FIG. 5 as shown by the block A or any other method as previously described.

Any variations of the algorithm outlined by the method 1200 are also contemplated, including incrementally varying an elevational angle and comparing it to previous elevational angles until the corresponding elevational presence score plateaus or decreases, whereupon the elevational angle with the optimal score may be selected.

Figure 13:
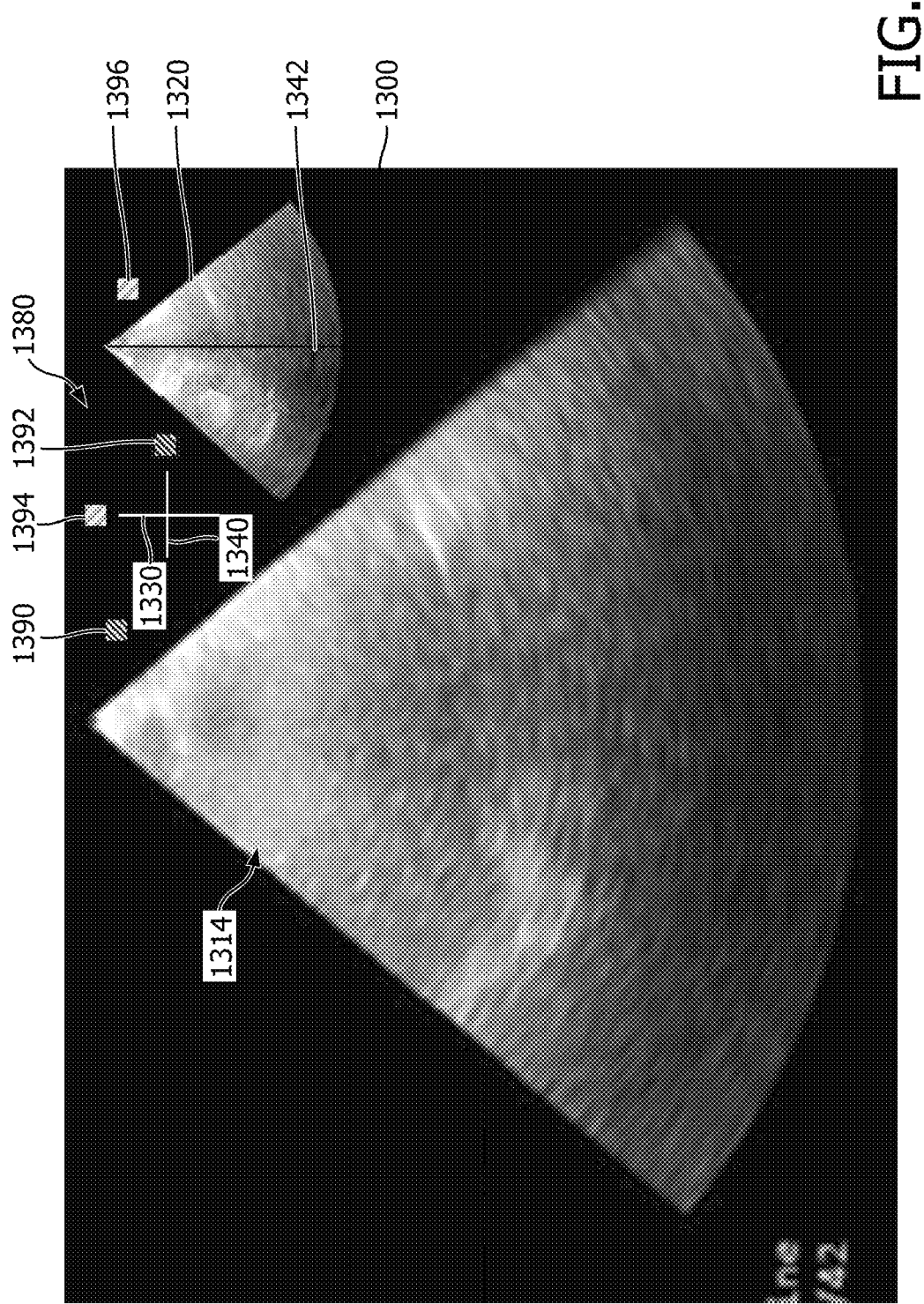
FIG. 13 is a diagrammatic view of a graphical user interface illustrating an ultrasound image obtained with a corresponding elevational angle, according to aspects of the present disclosure.

FIG. 13 is a diagrammatic view of a graphical user interface 1300 illustrating an ultrasound image obtained with a corresponding elevational angle, according to aspects of the present disclosure. FIG. 13 depicts an ultrasound image 1310 which may have been obtained with a default elevational angle, as shown by various indicators within the graphical user interface 1300. It is noted that the images shown and described with reference to FIG. 13 as well as FIG. 14 may be ultrasound images obtained with a three-dimensional ultrasound probe, or a probe including a two-dimensional transducer array or a matrix array.

Figure 14:
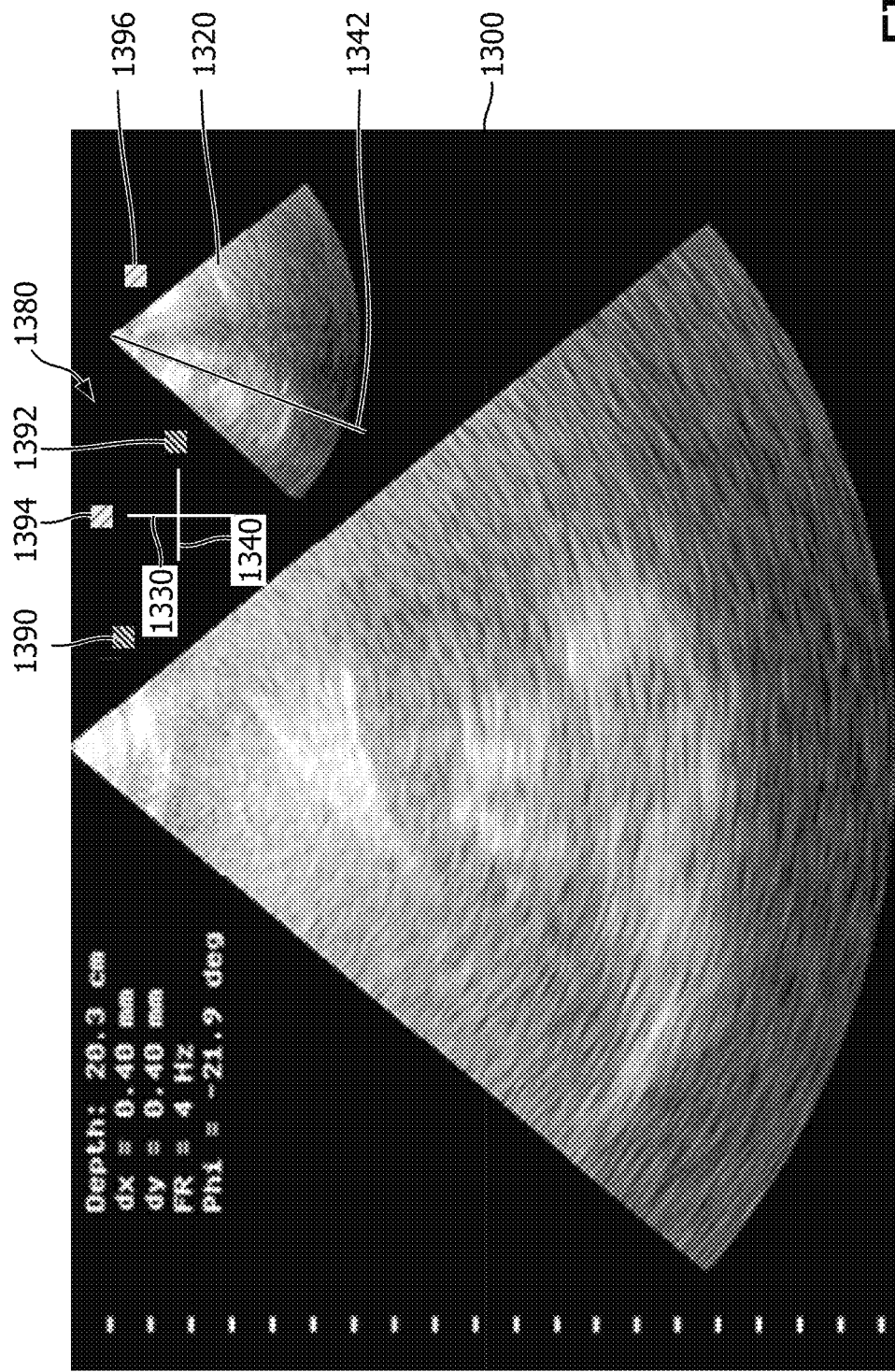
FIG. 14 is a diagrammatic view of a graphical user interface illustrating an ultrasound image obtained with a corresponding elevational angle, according to aspects of the present disclosure.

Graphical user interface 1300 includes an additional ultrasound image 1320. In some examples, the ultrasound image 1310 and the ultrasound image 1320 are orthogonal or perpendicular to one another. In this way, the indicator 1342 displayed overlaid over the image 1320 may illustrate for a user the elevational angle of the image 1310. It is noted, that, while the image 1310 shown and described with reference to FIG. 13 and the image 1410 shown and described with reference to FIG. 14 are described as having been obtained at an elevational angle, these images, or any similar images may be obtained at any suitable type of beam steering angle, including an elevational angle or a lateral angle, or any other type of angle. In this way, the ultrasound image 1320 may be obtained at a beam steering angle that is different from the beam steering angle of the images 1310 or 1410. For example, in the position shown, the indicator 1342 may illustrate a default elevational angle. This default elevational angle may correspond to an angle of 0 degrees, whereas a positive elevational angle may correspond to adjusting the angle of propagation ultrasound pulses in an upward direction relative to the ultrasound imaging probe and a negative elevational angle may correspond to adjusting the angle of propagation of ultrasound pulses in a downward direction relative to the ultrasound imaging probe.

Any of the indicators 1390, 1392, 1394, and/or 1396 may serve as reference indicators corresponding to directions relative to the ultrasound imaging probe. For example, the indicators 1392 and 1390 may correspond to a lateral direction of the ultrasound imaging probe. In one example, the indicators 1392 and 1390 may refer to a direction of propagation to the right of the lateral plane respective to the ultrasound imaging probe. In other examples, the indicators 1392 and 1390 may refer to a direction propagating to the left. Similarly, the indicators 1394 and 1396 may serve as reference indicators corresponding to directions relative to the ultrasound imaging probe in an elevational direction. For example, the indicators 1394 and 1396 may correspond to an upward elevational direction relative to the probe or a downward elevational direction relative to the probe.

In some examples, the ultrasound imaging probe may include a marker or other indicator on the housing of the probe on one lateral side of the probe. This marker or indicator on the housing of the probe may correspond to the indicators 1390 and/or 1392. The indicators 1390 and 1392 may then illustrate for an ultrasound imaging system user the orientation of the ultrasound imaging probe during acquisition of the corresponding image. As an example, if the indicator 1390 corresponds to a right lateral side of the ultrasound imaging probe, the indicator 1390 may be placed next to the image 1310 in such a way so as to show that the right side of the imaging probe corresponds to the right side of the image 1310, as shown in FIG. 13.

Similarly, the indicator 1396 may correspond to the image 1320 and may identify an elevational direction of the image 1320. For example, in an embodiment in which the indicators 1394 and 1396 correspond to an upward elevational direction of the ultrasound imaging probe, the indicator 1396 positioned next to the image 1320 may indicate that that side of the image 1320 is an upward elevational direction of the probe or image 1320. In that sense, a position of the indicator 1342 closer to the indicator 1396 may indicate an elevational angle that is upward relative to the probe. Similarly, a position of the indicator 1342 farther away from the indicator 1396 or closer to the side opposite the indicator 1396 of the image 1320 may indicate an elevational angle that is downward relative to the probe.

An imaging plane graphic 1380 is shown within the graphical user interface. The imaging plane graphic 1380 includes an axis 1330 and an axis 1340, which are also shown within the graphical user interface 1300. The imaging plane graphic 1380 may provide an additional view or graphical representation of the elevational angle of the image 1310. For example, as the elevational angle is adjusted to be different from the default angle, the indicator 1342 may be moved to different locations within the image 1320 and a corresponding indicator may be displayed along the axis 1330 corresponding to the different elevational angle (e.g., the indicator 1440 of FIG. 14 described hereafter). In this way, the axis 1330 may illustrate an elevational axis wherein the indicator 1394 indicates an upward elevational angle direction and the other end of the axis 1330 corresponds to a downward elevational angle. Similarly, the axis 1340 may represent a lateral axis wherein the indicator 1392 represents a right lateral direction relative to the imaging probe and the other end of the axis 1340 represents a left lateral direction.

The ultrasound image 1310 shown in FIG. 13 may correspond to an elevational angle that has not been optimized. For example, the image 1310 may display aspects of an anatomical feature which show a suboptimal elevational presence of the anatomical feature. For example, the anatomical feature may be of a size, including a diameter, cross sectional area, circumference, or any other dimension, which is different from an expected size. As explained previously, a suboptimal elevational presence may also be determined based on relative sizes of anatomical features within the same view.

FIG. 14 is a diagrammatic view of a graphical user interface 1300 illustrating an ultrasound image obtained with a corresponding elevational angle, according to aspects of the present disclosure. The graphical user interface 1300 as shown in FIG. 14 may correspond to a graphical user interface displayed to a user after an elevational angle has been adjusted.

For example, the ultrasound image 1410 shown in FIG. 14 may be an image received by the processor circuit after the elevational angle has been adjusted. As previously described, the image 1410 may be obtained according to an elevational angle which was automatically selected, for example, according to the steps of the method 1200 of FIG. 12. For example, the processor circuit (e.g., the processor circuit 210 of FIG. 2) may be configured to output a signal to a beamformer (e.g., the beamformer 114 of FIG. 1) in communication with the processor circuit to adjust the beam steering angle of the probe to acquire the image 1410. The adjustment in the elevational angle may be signified to a user both by a shift in the position of the indicator 1342, and the display of a new indicator 1440. As previously explained with reference to FIG. 13, the indicator 1342 may be overlaid over the image 1320 (which is orthogonal to the image 1410 and which may correspond to an elevational plane) to display to a user the elevational angle of the image 1410. As shown in FIG. 14, the indicator 1342 has been moved away from the indicator 1396. This may indicate to a user a decrease in the elevational angle of the ultrasound imaging system. In some embodiments, the new elevational angle corresponding to the image 1410 may result in higher image quality.

Similarly, the indicator 1440 shown overlaid over the axis 1330 of the imaging plane graphic 1380 is positioned along the axis 1330 in such a way as to illustrate the elevational angle. Just as the indicator 1342 is moved in a direction away from the indicator 1396, the indicator 1440 is placed along the axis 1330 away from the indicator 1394, illustrating a negative elevational angle.

Figure 15:
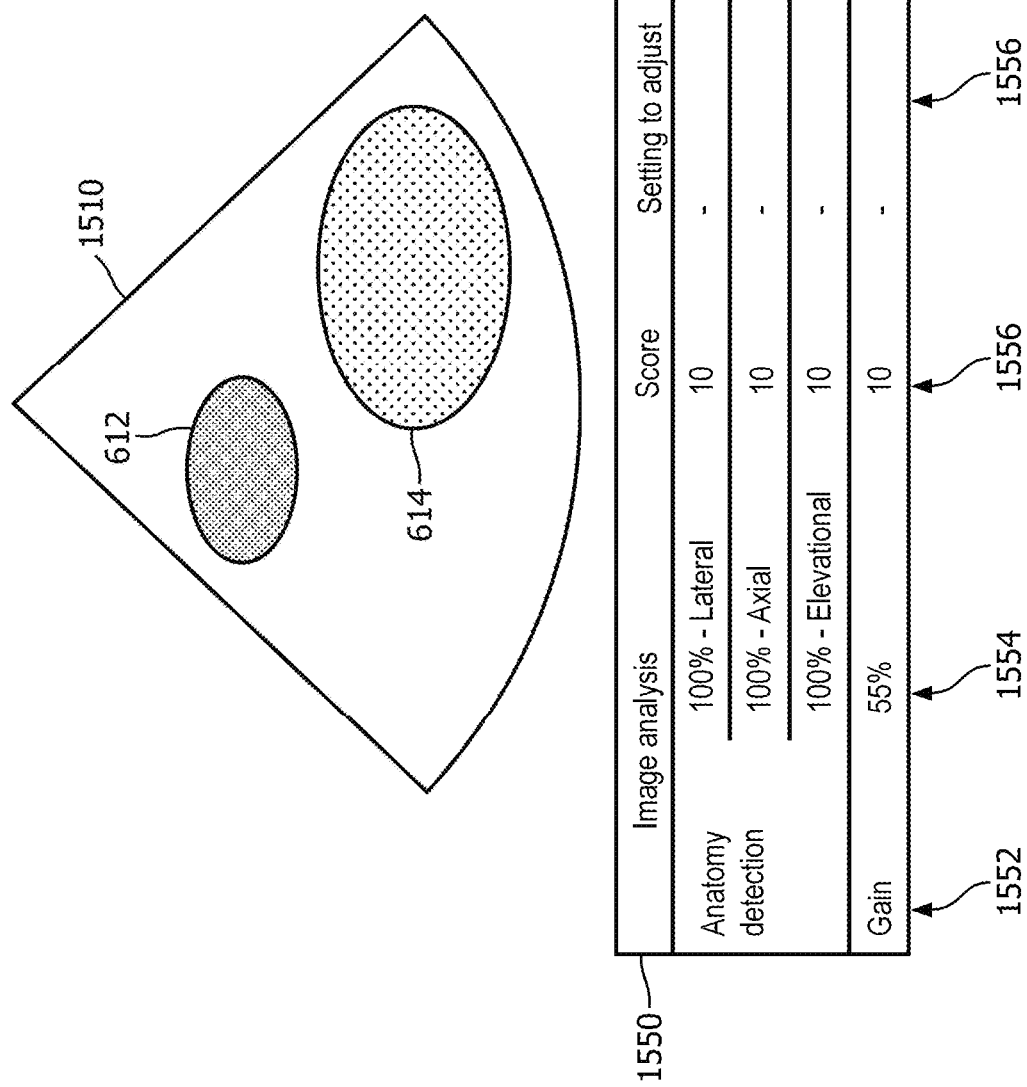
FIG. 15 is a diagrammatic view of an ultrasound image with automatically calculated measurements, scores, and setting adjustments, according to aspects of the present disclosure.

FIG. 15 is a diagrammatic view of an ultrasound image 1510 with automatically calculated measurements, scores, and setting adjustments, according to aspects of the present disclosure. The examples shown in FIG. 15 may illustrate an ultrasound image received after ultrasound image parameters have been adjusted to optimal parameters to maximize the image quality of received images.

For example, referring again to FIG. 5, the image 1510 may have been received at step 510 of the method 500 after the processor circuit has performed any steps of the method 500 or any of the methods or procedures described with reference to FIG. 5-12. In some examples, the processor circuit 210 may be configured to perform the steps of the method 500 again to ensure that the settings of the ultrasound imaging system are optimized.

As shown in FIG. 15, the image 1510 includes depictions of the anatomical feature 612 and the anatomical feature 614. As shown, both the anatomical feature 612 and the anatomical feature 614 are not cut off by any of the image borders of the image 1510. This may lead to optimal anatomy detection measurements. At step 530, and as shown in the columns 1552 and 1554 of the table 1550, the processor circuit may determine that the lateral presence of the anatomical feature 614, for example, is 100%. Similarly, the processor circuit may determine that the axial presence of the feature 614 is 100% and that the elevational presence of the feature is at 100% Similarly, the processor circuit 210 may measure the saturation or gain of the image 1510 and determine that the gain measurement corresponds to 55%, or an optimal level of saturation. Based on these optimized measurements, the processor circuit 210 may assign a score of 10 to each of these measurements, as shown by the column 1556. In this example, at the step 550 of the method 500, referring again to FIG. 5, the processor circuit 210 may determine that the score of the image 1510 satisfies a corresponding threshold score and that no ultrasound imaging settings are to be adjusted, as shown by the setting adjustment column 1556. In this scenario, at the step 550, the processor circuit 210 may optionally store the image 1510 in a memory and may revert back to the step 510 to continue receiving ultrasound images in, for example, a live imaging procedure.

Figure 16:
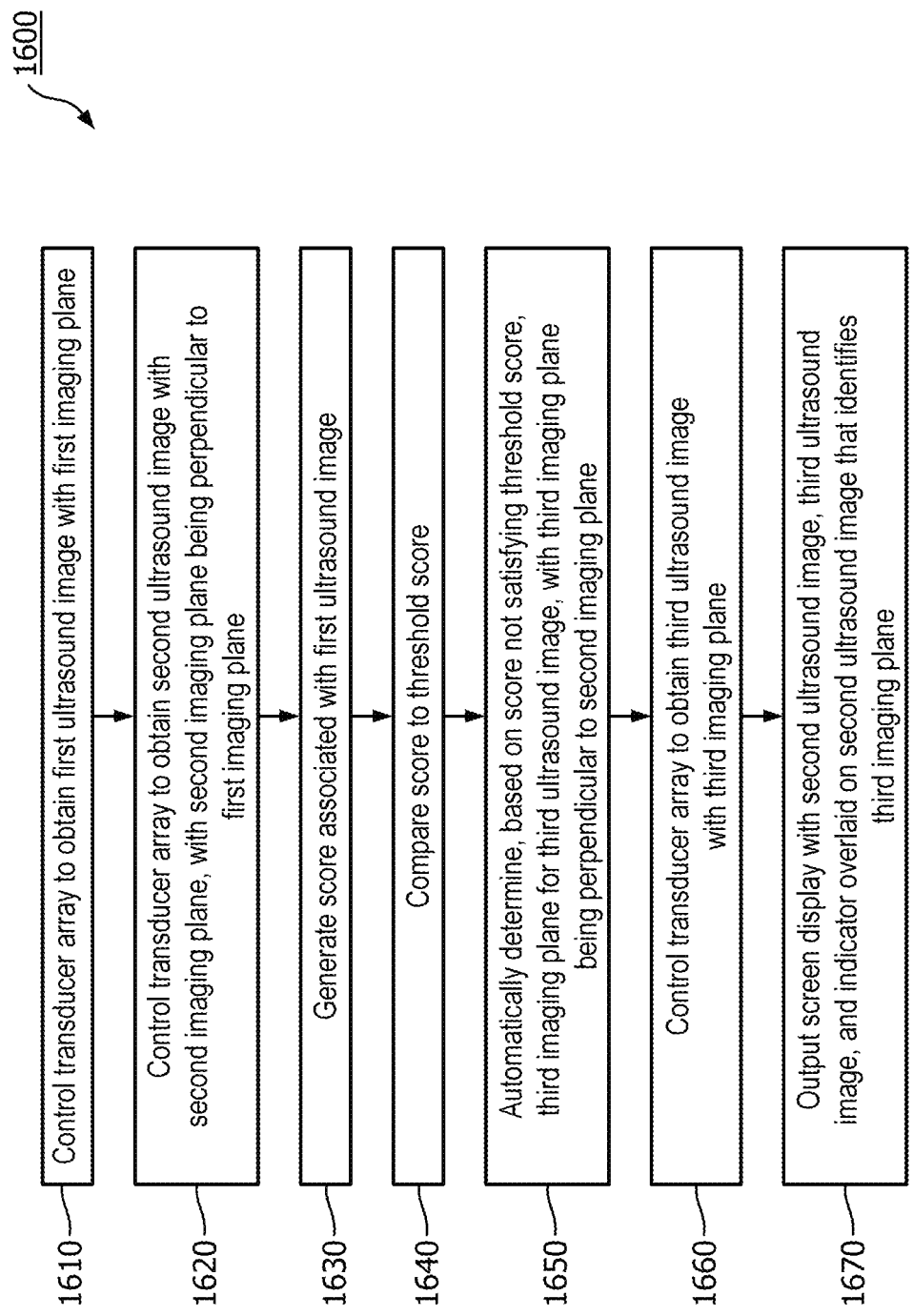
FIG. 16 is a flow diagram of a method of identifying an elevational angle of an ultrasound image and displaying an indication of the elevational angle on an orthogonal ultrasound image, according to aspects of the present disclosure.

FIG. 16 is a flow diagram of a method 1600 of identifying an elevational angle of an ultrasound image and displaying an indication of the elevational angle on an orthogonal ultrasound image, according to aspects of the present disclosure. As illustrated, the method 1600 includes a number of enumerated steps, but aspects of the method 1600 may include additional steps before, after, or in between the enumerated steps. In some aspects, one or more of the enumerated steps may be omitted, performed in a different order, or performed concurrently. The steps of the method 1600 can be carried out by any suitable component within the system 100 and all steps need not be carried out by the same component. In some aspects, one or more steps of the method 1600 can be performed by, or at the direction of, a processor circuit, including, e.g., the processor 116 (FIG. 1), the processor 134 (FIG. 1), the processor 260 (FIG. 2) or any other suitable component.

At step 1610, the method 1600 includes controlling a transducer array to obtain a first ultrasound image with a first imaging plane. The first imaging plane may correspond to an elevational angle. In some examples, the first imaging plane may correspond to an elevational view of the subject anatomy.

At step 1620, the method 1600 includes controlling the transducer array to obtain a second ultrasound image with a second imaging plane, wherein the second imaging plane and the first imaging plane are perpendicular. In some examples, the second imaging plane may be a lateral view of the subject anatomy.

At step 1630, the method 1600 includes generating a score associated with the first ultrasound image. In some aspects, the score can be generated using a machine learning algorithm, such as a machine learning algorithm that is trained using a reference ultrasound image. In some aspects, step 1630 may include comparing the first ultrasound image to a reference ultrasound image. The comparison of the first ultrasound image to the reference ultrasound image may be performed by the processor circuit according to an image processing algorithm, a machine learning algorithm, or any other suitable algorithm, method, or process, as described herein. In some aspects, the step 1630 may include generating a score associated with the first ultrasound image based on the comparison of the first ultrasound image with the reference ultrasound image. The score may be of any suitable type, including a value within a range of values. In some examples, the processor circuit may identify multiple scores. For example, a score may be determined associated with each of the parameters described herein. It is noted that, in some aspects, generating the first score can be based on a comparison of the first ultrasound image with the reference ultrasound image. Any of steps 1630-1650 may be implemented as a machine learning algorithm trained with one or more reference images. For example, the AI/machine learning algorithm is trained using the reference ultrasound image (e.g., many reference ultrasound images). In some instances, inference of the AI/machine learning algorithm (when the AI/machine learning algorithm is implemented with the first ultrasound image) can be considered a comparison between the first ultrasound image and the reference ultrasound image(s) because the AI/machine learning algorithm is providing an output (e.g., the first score) based on the training with the reference ultrasound image(s).

At step 1640, the method 1600 includes comparing the score to a threshold score. In some examples, step 1640 may include comparing multiple scores to corresponding thresholds.

At step 1650, the method 1600 includes automatically determining a third imaging plane for a third ultrasound image based on an anatomical feature of a subject anatomy in the first ultrasound image. The second imaging plane and the third imaging plane are perpendicular. In some examples, the third imaging plane may correspond to an elevational view of the subject anatomy. The third imaging plane may correspond to an elevational angle that is different from the first imaging plane. Both the first imaging plane and the third imaging plane may be perpendicular to the second imaging plane. At step 1660, the method 1600 includes controlling the transducer array to obtain the third ultrasound image with the third imaging plane.

At step 1670, the method 1600 includes outputting, to a display in communication with the processor, a screen display including the second ultrasound image, the third ultrasound image, and an indicator overlaid on the second ultrasound image and configured to identify the third imaging plane. In some examples, the screen display may also include the first ultrasound image.

Figure 17:
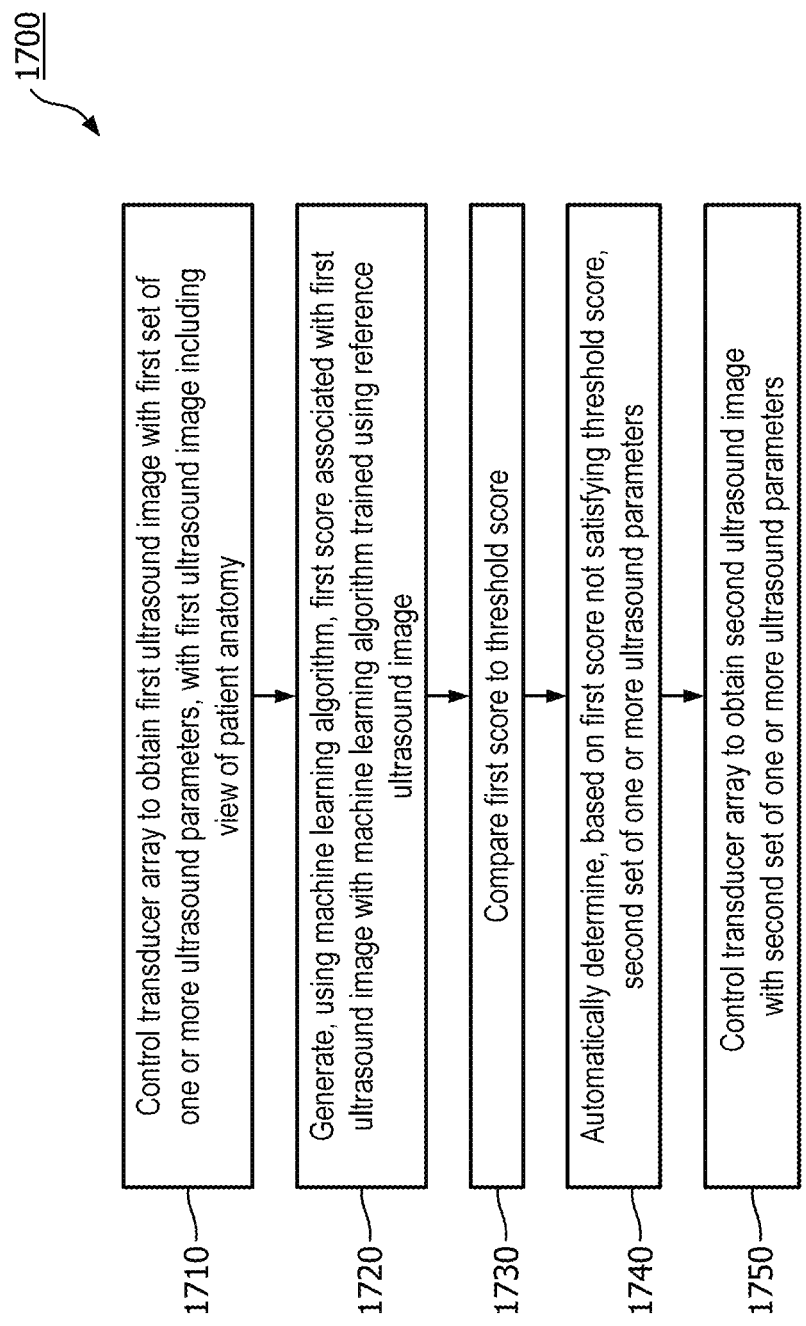
FIG. 17 is a flow diagram of a method of automatically adjusting ultrasound parameters to improve image quality, according to aspects of the present disclosure.

FIG. 17 is a flow diagram of a method of automatically adjusting ultrasound parameters to improve image quality, according to aspects of the present disclosure. As illustrated, the method 1700 includes a number of enumerated steps, but aspects of the method 1700 may include additional steps before, after, or in between the enumerated steps. One or more of the enumerated steps may be omitted, performed in a different order, or performed concurrently. The steps of the method 1700 can be carried out by any suitable component within the system 100 and all steps need not be carried out by the same component. In some aspects, one or more steps of the method 1700 can be performed by, or at the direction of, a processor circuit, including, e.g., the processor 116 (FIG. 1), the processor 134 (FIG. 1), the processor 260 (FIG. 2) or any other suitable component.

At step 1710, the method 1700 includes controlling a transducer array of an ultrasound imaging system to obtain a first ultrasound image with a first set of one or more ultrasound parameters. The first ultrasound image may include a view of a subject anatomy. The ultrasound parameters may include a depth setting, a lateral angle setting, a beam steering angle setting (e.g., an elevational angle setting), a gain setting, or any other setting.

At step 1720, the method 1700 includes generating a first score associated with the first ultrasound image. For example, the first score can be generated using a machine learning algorithm that is trained using a reference ultrasound image. Step 1720 may include comparing the first ultrasound image to a reference ultrasound image. The comparison of the first ultrasound image to the reference ultrasound image may be performed by the processor circuit according to an image processing algorithm, a machine learning algorithm, or any other suitable algorithm, method, or process, as described herein. The step 1720 may include generating a first score associated with the first ultrasound image based on the comparison of the first ultrasound image with the reference ultrasound image. The score may be of any suitable type, including a value within a range of values. In some examples, the processor circuit may identify multiple scores. A score may be determined associated with each of the parameters described herein. It is noted that, in some aspects, generating the first score can be based on a comparison of the first ultrasound image with the reference ultrasound image. Any of steps 1720-1740 may be implemented as a machine learning algorithm trained with one or more reference images. For example, the AI/machine learning algorithm is trained using the reference ultrasound image (e.g., many reference ultrasound images). In some instances, inference of the AI/machine learning algorithm (when the AI/machine learning algorithm is implemented with the first ultrasound image) can be considered a comparison between the first ultrasound image and the reference ultrasound image(s) because the AI/machine learning algorithm is providing an output (e.g., the first score) based on the training with the reference ultrasound image(s). The step 1720 may additionally include identifying an anatomical feature of the subject anatomy within the first ultrasound image. The feature may include any of those features described herein.

At step 1730, the method 1700 includes comparing the first score to a threshold score. In some examples, step 1730 may include comparing multiple scores to corresponding thresholds.

At step 1740, the method 1700 includes automatically determining, based on the first score not satisfying the threshold score, a second set of one or more ultrasound parameters. At step 1740, the processor circuit may determine that the image quality of the first ultrasound image is not sufficient. The processor circuit may, therefore, determine the second set of ultrasound parameters based on a prediction of parameters which may increase the image quality of received ultrasound images.

At step 1750, the method 1700 includes controlling the transducer array to obtain a second ultrasound image with the second set of one or more ultrasound parameters. The processor circuit may then perform any of the steps of the method 1700 with respect to the second ultrasound image according to a recursive process. In some examples, the processor circuit may not perform these steps according to a periodic process.

All or parts of the method 500 (FIG. 5), the method 900 (FIG. 9), the method 1000 (FIG. 10), the method 1100 (FIG. 11), the method 1200 (FIG. 12), the method 1600 (FIG. 16), and/or the method 1700 (FIG. 17) can be restatements or reformulations of the same method. For example, one or more steps of the method 500 (FIG. 5), the method 900 (FIG. 9), the method 1000 (FIG. 10), the method 1100 (FIG. 11), the method 1200 (FIG. 12), the method 1600 (FIG. 16), and/or the method 1700 (FIG. 17) can be combined and/or replaced with one or another.

The steps of the method 500 (FIG. 5), the method 900 (FIG. 9), the method 1000 (FIG. 10), the method 1100 (FIG. 11), the method 1200 (FIG. 12), the method 1600 (FIG. 16), and/or the method 1700 (FIG. 17) may include instructions stored on a non-transitory computer readable medium, such as the memory 264 (FIG. 2). In that regard, a processor, such as the processor 260 (FIG. 2), can execute instructions stored on the non-transitory computer readable medium to perform any or all of steps of the method. For example, the method may be implemented as part of a system, device, apparatus, and/or as instructions stored on a computer readable medium for execution by a processor or a computer including the processor.

Persons skilled in the art will recognize that the apparatus, systems, and methods described above can be modified in various ways. Accordingly, persons of ordinary skill in the art will appreciate that the aspects encompassed by the present disclosure are not limited to the particular exemplary aspects described above. In that regard, although illustrative aspects have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure. In the claims, any reference signs placed between parentheses shall not be construed as limiting the claim. The word "comprising" does not exclude the presence of elements or steps other than those listed in a claim. The word "a" or "an" preceding an element does not exclude the presence of a plurality of such elements. The invention may be implemented by means of hardware comprising several distinct elements, and/or by means of a suitably programmed processor. In the device claim enumerating several means, several of these means may be embodied by one and the same item of hardware. Measures recited in mutually different dependent claims may advantageously be used in combination.

The invention claimed is:

1. An ultrasound system, comprising:
a processor configured for communication with a transducer array of an ultrasound imaging probe, wherein the processor is configured to:
control the transducer array to obtain a first ultrasound image with a first set of one or more ultrasound parameters, wherein the first ultrasound image comprises an anatomical feature;
generate, using a machine learning algorithm, a first score associated with the first ultrasound image, wherein the machine learning algorithm is trained using a reference ultrasound image, wherein the first score is based on a completeness of view measurement of the anatomical feature and comprises at least one of a lateral presence measurement, an axial presence measurement, or an elevational presence measurement;
compare the first score to a threshold score;
automatically determine, based on the first score not satisfying the threshold score, a second set of one or more ultrasound parameters; and
control the transducer array to obtain a second ultrasound image with the second set of one or more ultrasound parameters.

2. The ultrasound system of claim 1,
wherein the processor is configured to identify the anatomical feature, and
wherein the first score is further based on a measurement of gain of the first ultrasound image.

3. The ultrasound system of claim 1, wherein the one or more ultrasound parameters comprise at least one of:
a depth parameter;
a lateral view parameter;
an angle of an elevational plane; and
a gain parameter.

4. The ultrasound system of claim 1, wherein the processor is configured to determine a second score associated with the second ultrasound image.

5. The ultrasound system of claim 4,
wherein, based on the second score satisfying the threshold value, the processor is configured to store the second ultrasound image in a memory in communication with the processor, or
wherein, based on the second score not satisfying the threshold value, the processor is configured to:
automatically determine a third set of one or more ultrasound parameters; and
control the ultrasound transducer array to obtain a third ultrasound image.

6. The ultrasound system of claim 1, wherein the first ultrasound image is one of a plurality of ultrasound images obtained during live imaging.

7. The ultrasound system of claim 6, wherein the processor is further configured to determine a score corresponding to each of the plurality of ultrasound images.

8. The ultrasound system of claim 6,
wherein the second ultrasound image is one of the plurality of ultrasound images,
wherein the processor is further configured to automatically determine a second score associated with the second ultrasound image,
wherein the first ultrasound image and the second ultrasound image are separated by a predetermined time period.

9. The ultrasound system of claim 1, wherein the processor is further configured to output, to a display in communication with the processor, at least one of the first ultrasound image or the second ultrasound image.

10. An ultrasound system, comprising:
a processor configured for communication with a transducer array and a display,
wherein the processor is configured to:
control the transducer array to obtain a first ultrasound image with a first imaging plane;
control the transducer array to obtain a second ultrasound image with a second imaging plane, wherein the second imaging plane and the first imaging plane are perpendicular;

generate a score associated with the first ultrasound image, wherein the first score is based on a completeness of view measurement for the first imaging plane and comprises at least one of a lateral presence measurement, an axial presence measurement, or an elevational presence measurement;

compare the score to a threshold score;

automatically determine, based on the score not satisfying the threshold score, a third imaging plane for a third ultrasound image, wherein the second imaging plane and the third imaging plane are perpendicular;

control the transducer array to obtain the third ultrasound image with the third imaging plane; and output, to the display, a screen display comprising:
the second ultrasound image;
the third ultrasound image; and
an indicator overlaid on the second ultrasound image and configured to identify the third imaging plane.

11. The ultrasound system of claim 10,
wherein a beam steering angle of the third imaging plane is different than the beam steering angle of the first ultrasound image, and
wherein, to control the transducer array to obtain the third ultrasound image, the processor is configured to output a signal to change the beam steering angle of the first ultrasound image to the beam steering angle of the third imaging plane.

12. The ultrasound system of claim 10,
wherein the screen display further comprises an imaging plane graphic,
wherein the imaging plane graphic is configured to identify the first imaging plane, the second imaging plane, and the third imaging plane,
wherein the imaging plane graphic comprises a first graphical representation of the first imaging plane, a second graphical representation of the second imaging plane, and a third graphical representation of the third imaging plane,
wherein the first graphical representation and the second graphical representation are perpendicular, and
wherein the second graphical representation and the third graphical representation are perpendicular.

13. The ultrasound system of claim 12, wherein a position of the first graphical representation and a position of the third graphical representation are spaced along the second graphical representation such that the position of the first graphical representation and the position of the third graphical representation represent that the beam steering angle of the first imaging plane is different than the beam steering angle of the third ultrasound image.

14. A method, comprising:
controlling a transducer array to obtain a first ultrasound image with a first set of one or more ultrasound parameters, wherein the first ultrasound image comprises an anatomical feature;

generating, using a machine learning algorithm, a score associated with the first ultrasound image, wherein the machine learning algorithm is trained using a reference ultrasound image, wherein the first score is based on a completeness of view measurement of the anatomical feature and comprises at least one of a lateral presence measurement, an axial presence measurement, or an elevational presence measurement;

comparing the score to a threshold score;

automatically determining, based on the score not satisfying the threshold score, a second set of one or more ultrasound parameters; and controlling the transducer array to obtain a second ultrasound image with the second set of one or more ultrasound parameters.

* * * * *